(12) United States Patent
Wang

(10) Patent No.: US 11,118,233 B2
(45) Date of Patent: Sep. 14, 2021

(54) BTK MUTATION AND IBRUTINIB RESISTANCE

(71) Applicant: The University of Chicago, Chicago, IL (US)

(72) Inventor: Y. Lynn Wang, Chicago, IL (US)

(73) Assignee: The University of Chicago, Chicago, IL (US)

( * ) Notice: Subject to any disclaimer, the term of this patent is extended or adjusted under 35 U.S.C. 154(b) by 74 days.

(21) Appl. No.: 16/302,015

(22) PCT Filed: May 18, 2017

(86) PCT No.: PCT/US2017/033354
§ 371 (c)(1),
(2) Date: Nov. 15, 2018

(87) PCT Pub. No.: WO2017/201302
PCT Pub. Date: Nov. 23, 2017

(65) Prior Publication Data
US 2019/0153543 A1 May 23, 2019

Related U.S. Application Data

(60) Provisional application No. 62/338,311, filed on May 18, 2016.

(51) Int. Cl.
| | | |
|---|---|---|
| C12Q 1/68 | (2018.01) | |
| C12Q 1/6886 | (2018.01) | |
| G01N 33/573 | (2006.01) | |
| C12N 9/12 | (2006.01) | |

(52) U.S. Cl.
CPC ........... C12Q 1/6886 (2013.01); C12N 9/12 (2013.01); G01N 33/573 (2013.01); C12Q 2600/106 (2013.01); C12Q 2600/156 (2013.01); G01N 2333/912 (2013.01); G01N 2800/52 (2013.01)

(58) Field of Classification Search
None
See application file for complete search history.

(56) References Cited

U.S. PATENT DOCUMENTS

| | | |
|---|---|---|
| 5,538,848 A | 7/1996 | Livak et al. |
| 5,639,606 A | 6/1997 | Willey |
| 5,643,765 A | 7/1997 | Willey |
| 5,695,934 A | 12/1997 | Brenner |
| 5,714,330 A | 2/1998 | Brenner et al. |
| 5,750,341 A | 5/1998 | MacEvicz |
| 5,846,717 A | 12/1998 | Brow et al. |
| 5,861,510 A | 1/1999 | Piscopio et al. |
| 5,863,949 A | 1/1999 | Robinson et al. |
| 5,876,978 A | 3/1999 | Willey et al. |
| 5,985,557 A | 11/1999 | Prudent et al. |
| 5,994,069 A | 11/1999 | Hall et al. |
| 6,001,567 A | 12/1999 | Brow et al. |
| 6,090,543 A | 7/2000 | Prudent et al. |
| 6,306,597 B1 | 10/2001 | MacEvicz |
| 6,432,360 B1 | 8/2002 | Church |
| 6,485,944 B1 | 11/2002 | Church et al. |
| 6,511,803 B1 | 1/2003 | Church et al. |
| 6,787,308 B2 | 9/2004 | Balasubramanian et al. |
| 6,833,246 B2 | 12/2004 | Balasubramanian |
| 2003/0040461 A1 | 2/2003 | McAtee |
| 2013/0273063 A1 | 10/2013 | Han et al. |

FOREIGN PATENT DOCUMENTS

| | | |
|---|---|---|
| EP | 0606046 | 7/1994 |
| EP | 0780386 | 6/1997 |
| EP | 0818442 | 1/1998 |
| EP | 0931788 | 7/1999 |
| EP | 1004578 | 5/2000 |
| WO | WO 1990/05719 | 5/1990 |
| WO | WO 1996/27583 | 9/1996 |
| WO | WO 1996/33172 | 10/1996 |
| WO | WO 1998/03516 | 1/1998 |
| WO | WO 1998/07697 | 2/1998 |
| WO | WO 1998/30566 | 7/1998 |
| WO | WO 1998/33768 | 8/1998 |
| WO | WO 1998/34915 | 8/1998 |
| WO | WO 1998/34918 | 8/1998 |
| WO | WO 1999/07675 | 2/1999 |
| WO | WO 1999/29667 | 6/1999 |
| WO | WO 1999/52889 | 10/1999 |
| WO | WO 1999/52910 | 10/1999 |
| WO | WO 2000/018957 | 4/2000 |
| WO | WO 2006/084132 | 8/2006 |
| WO | WO 2014018567 | * 1/2014 |

OTHER PUBLICATIONS

Adessi et al., Solid phase DNA amplification: characterisation of primer attachment and amplification mechanisms. Nucleic Acids Res. Oct. 15, 2000;28(20):E87.
Bennett et al., Toward the $1,000 human genome. Pharmacogenomics. Jun. 2005;6(4):373-82.
Binnerts et al., SNS-062 is a potent noncovalent BTK inhibitor with comparable activity agains wild type BTK and BTK with an acquired resistance mutation. Abs. C186, AACR-CNI-EORTC International Conference: Molecular Targets and Cancer Therapeutics, Nov. 5-9, 2015, Boston, MA, 2 pages.
Brenner et al., Gene expression analysis by massively parallel signature sequencing (MPSS) on microbead arrays. Nat Biotechnol. Jun. 2000;18(6):630-4.
Burger et al., Clonal evolution in patients with chronic lymphocytic leukemia (CLL) developing resistance to BTK inhibition. Nat Commun. May 20, 2016;7:11589.

(Continued)

*Primary Examiner* — Jehanne S Sitton
(74) *Attorney, Agent, or Firm* — Casimir Jones, S.C.; David W. Staple

(57) ABSTRACT

Provided herein are mutations in Bruton's Tyrosine Kinase (BTK) that confer resistance to treatment with a BTK inhibitors, such as Ibrutinib, and compositions and methods for the treatment, diagnosis, and characterization of BTK-inhibitor-resistant cancers.

14 Claims, 7 Drawing Sheets
Specification includes a Sequence Listing.

(56) References Cited

OTHER PUBLICATIONS

Byrd et al., Ibrutinib in relapsed chronic lymphocytic leukemia. N Engl J Med. Sep. 26, 2013;369(13):1278-9.

Cheng et al., Functional characterization of BTK(C481S) mutation that confers ibrutinib resistance: exploration of alternative kinase inhibitors. Leukemia. Apr. 2015;29(4):895-900.

Davis et al., Chronic active B-cell-receptor signalling in diffuse large B-cell lymphoma. Nature. Jan. 7, 2010;463(7277):88-92.

Furman et al., Ibrutinib resistance in chronic lymphocytic leukemia. N Engl J Med. Jun. 12, 2014;370(24):2352-4.

Grazini et al., Identification of a Btk mutation in a dysgammaglobulinemic patient with reduced B cells: XLA diagnosis or not? Clin Immunol. Sep. 2008;128(3):322-8.

Hashimoto et al., Identification of the SH2 domain binding protein of Bruton's tyrosine kinase as BLNK—functional significance of Btk-SH2 domain in B-cell antigen receptor-coupled calcium signaling. Blood. Oct. 1, 1999;94(7):2357-64.

Huang et al., Solution structure and phosphopeptide binding of the SH2 domain from the human Bruton's tyrosine kinase. J Biomol NMR. Sep. 2006;36(1):73-8.

Hyvonen et al., Structure of the PH domain and Btk motif from Bruton's tyrosine kinase: molecular explanations for X-linked agammaglobulinaemia. EMBO J. Jun. 16, 1997;16(12):3396-404.

Jain et al., Outcomes of patients with chronic lymphocytic leukemia after discontinuing ibrutinib. Blood. Mar. 26, 2015;125(13):2062-7.

Komarova et al., Evolution of ibrutinib resistance in chronic lymphocytic leukemia (CLL). Proc Natl Acad Sci U S A. Sep. 23, 2014;111(38):13906-11.

Maclean et al., Application of 'next-generation' sequencing technologies to microbial genetics. Nat Rev Microbiol. Apr. 2009;7(4):287-96.

Maddocks et al., Etiology of ibrutinib therapy discontinuation and outcomes in patients with chronic lymphocytic leukemia. JAMA Oncol. Apr. 2015;1(1):80-7.

Marcotte et al., Structures of human Bruton's tyrosine kinase in active and inactive conformations suggest a mechanism of activation for TEC family kinases. Protein Sci. Mar. 2010;19(3):429-39.

Margulies et al., Genome sequencing in microfabricated high-density picolitre reactors. Nature. Sep. 15, 2005;437(7057):376-80.

Mitra et al., Fluorescent in situ sequencing on polymerase colonies. Anal Biochem. Sep. 1, 2003;320(1):55-65.

Shendure et al., Accurate multiplex polony sequencing of an evolved bacterial genome. Science. Sep. 9, 2005;309(5741):1728-32.

Tzeng et al., Solution structure of the human BTK SH3 domain complexed with a proline-rich peptide from p120cbl.J Biomol NMR. Apr. 2000;16(4):303-12.

Voelkerding et al., Next-generation sequencing: from basic research to diagnostics. Clin Chem. Apr. 2009;55(4):641-58.

Woyach et al., Resistance mechanisms for the Bruton's tyrosine kinase inhibitor ibrutinib. N Engl J Med. Jun. 12, 2014;370(24):2286-94.

Zhang et al., Mechanisms of ibrutinib resistance in chronic lymphocytic leukaemia and non-Hodgkin lymphoma. Br J Haematol. Aug. 2015;170(4):445-56.

International Search Report and Written Opinion for PCT/US2017/033354, dated Sep. 29, 2017, 15 pages.

\* cited by examiner

A

B

SEQUENCE LISTING

<160> NUMBER OF SEQ ID NOS: 6

<210> SEQ ID NO 1
<211> LENGTH: 659
<212> TYPE: PRT
<213> ORGANISM: Homo sapiens

<400> SEQUENCE: 1

```
Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Glu Lys Ile Thr Cys Val
    50                  55                  60

Glu Thr Val Val Pro Glu Lys Asn Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
            100                 105                 110

Val Phe Ser Pro Thr Glu Glu Leu Arg Lys Arg Trp Ile His Gln Leu
        115                 120                 125

Lys Asn Val Ile Arg Tyr Asn Ser Asp Leu Val Gln Lys Tyr His Pro
    130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Ala Ala
        195                 200                 205

Ala Pro Val Ser Thr Ser Glu Leu Lys Lys Val Val Ala Leu Tyr Asp
    210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
            260                 265                 270

Glu Asp Ser Ile Glu Met Tyr Glu Trp Tyr Ser Lys His Met Thr Arg
        275                 280                 285

Ser Gln Ala Glu Gln Leu Leu Lys Gln Glu Gly Lys Glu Gly Gly Phe
    290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
            340                 345                 350

Ser Thr Ile Pro Glu Leu Ile Asn Tyr His Gln His Asn Ser Ala Gly
        355                 360                 365
```

```
Leu Ile Ser Arg Leu Lys Tyr Pro Val Ser Gln Gln Asn Lys Asn Ala
    370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                405                 410                 415

Lys Tyr Gly Lys Trp Arg Gly Gln Tyr Asp Val Ala Ile Lys Met Ile
                420                 425                 430

Lys Glu Gly Ser Met Ser Glu Asp Glu Phe Ile Glu Ala Lys Val
                435                 440                 445

Met Met Asn Leu Ser His Glu Lys Leu Val Gln Leu Tyr Gly Val Cys
450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
                500                 505                 510

Glu Ser Lys Gln Phe Leu His Arg Asp Leu Ala Ala Arg Asn Cys Leu
                515                 520                 525

Val Asn Asp Gln Gly Val Val Lys Val Ser Asp Phe Gly Leu Ser Arg
530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
                565                 570                 575

Lys Ser Asp Ile Trp Ala Phe Gly Val Leu Met Trp Glu Ile Tyr Ser
                580                 585                 590

Leu Gly Lys Met Pro Tyr Glu Arg Phe Thr Asn Ser Glu Thr Ala Glu
                595                 600                 605

His Ile Ala Gln Gly Leu Arg Leu Tyr Arg Pro His Leu Ala Ser Glu
610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
                645                 650                 655

Glu Glu Ser

<210> SEQ ID NO 2
<211> LENGTH: 11
<212> TYPE: DNA
<213> ORGANISM: Homo sapiens

<400> SEQUENCE: 2
cactgtatat t                                                      11

<210> SEQ ID NO 3
<211> LENGTH: 4
<212> TYPE: PRT
<213> ORGANISM: Homo sapiens

<400> SEQUENCE: 3

Val Thr Tyr Lys
1

<210> SEQ ID NO 4
```

```
<211> LENGTH: 11
<212> TYPE: DNA
<213> ORGANISM: Homo sapiens

<400> SEQUENCE: 4
cactgcatat t                                                           11

<210> SEQ ID NO 5
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 5
gagacagagg aagtgggacg                                                  20

<210> SEQ ID NO 6
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 6
gcaccacttc ctcctacaga                                                  20
```

BTK MUTATION AND IBRUTINIB RESISTANCE

FIELD

Provided herein are mutations in Bruton's Tyrosine Kinase (BTK) that confer resistance to treatment with a BTK inhibitors, such as Ibrutinib, and compositions and methods for the treatment, diagnosis, and characterization of BTK-inhibitor-resistant cancers.

BACKGROUND

Bruton's Tyrosine Kinase (BTK) is member of the Tec family of non-receptor tyrosine kinases that is critically important for the growth, differentiation and activation of B-cells, myeloid cells, and mast cells. The BTK gene is located at cytogenetic band Xq21.33-q22 and comprises 19 exons, spanning 37 kb, encoding the full length BTK protein. Mutations in BTK are known in humans.

BTK is essential to B-cell receptor (BCR) signaling and in knockout mouse models its mutation has a B cell-specific phenotype. BTK protein and mRNA are significantly over expressed in chronic lymphocytic leukemia (CLL) compared with normal B-cells. Although BTK is not always constitutively active in CLL cells, B-cell receptor (BCR) or CD40 signaling is accompanied by effective activation of this pathway. BTK activity is involved in the disease progression of B-cell malignancies, such as Non-Hodgkin's Lymphomas, such as chronic lymphocytic leukemia (CLL), mantle cell leukemia (MCL), follicular lymphoma (FL) and diffuse large B-cell lymphoma (DLBCL), and multiple myeloma (MM).

Ibrutinib (ibr), an inhibitor of BTK, has long been used to treat B-cell malignancies such as CLL, and has demonstrated high response rates in both relapsed/refractory and treatment naïve CLL. However, in some cases, ibrutinib treatment is discontinued due to progression of leukemia, or Richter Transformation (progression of CLL into an aggressive form of tumor with poor prognosis). Mutations within the kinase domain of BTK (e.g., at C481) disrupt ibrutinib binding and are the most common mechanism of ibrutinib resistance. Despite this, the role and mechanisms by which BTK mutations affect cancer relapse and Richter transformation remains unclear.

SUMMARY

Provided herein are mutations in Bruton's Tyrosine Kinase (BTK) that confer resistance to treatment with BTK inhibitors (e.g., covalent and/or non-covalent), such as Ibrutinib, and compositions and methods for the treatment, diagnosis, and characterization of BTK-inhibitor-resistant cancers.

In some embodiments, provided herein are methods for determining whether a subject is resistant or likely to become less responsive to therapy with a Bruton's Tyrosine Kinase (BTK) inhibitor, comprising: (a) testing a sample from the subject for the presence of a BTK biomarker comprising or encoding a modification at a position corresponding position 316 of the sequence set forth in SEQ ID NO: 1; and (b) characterizing the subject as resistant or likely to become less responsive to treatment BTK inhibitor if the subject has the modification. In some embodiments, the subject has been administered a BTK inhibitor for treatment of a cancer or is a potential candidate for treatment with a BTK inhibitor. In some embodiments, methods comprise testing the sample for the presence of the 481r BTK biomarkers of resistance or risk of becoming less responsive to therapy with a Bruton's Tyrosine Kinase (BTK) inhibitor, such as those present in the pleckstrin homology (PH) domain, TEC homology (TH) domain, SRC homology 2 (SH2) domain, SRC homology 3 (SH3) domain, and kinase domain.

In some embodiments, provided herein are methods for optimizing the therapy of a subject receiving a BTK inhibitor for treatment of a cancer, comprising: (a) testing a sample from the subject to determine the presence or absence of a BTK biomarker comprising or encoding a modification at a position corresponding position 316 of the sequence set forth in SEQ ID NO: 1; and (b) discontinuing treatment with the BTK inhibitor if the subject has the modification or continuing treatment with the BTK inhibitor if the subject does not have the modification.

In some embodiments, provided herein are methods for selecting a subject for therapy with a second generation BTK inhibitor, comprising: (a) testing a sample from the subject to determine the presence or absence of a BTK biomarker comprising or encoding a modification at a position corresponding position 316 of the sequence set forth in SEQ ID NO: 1; and (b) characterizing the subject as a candidate for therapy with a second generation BTK inhibitor if the subject has the modification.

In some embodiments, provided herein are methods of treating cancer in a subject comprising: (a) testing the subject for the presence or absence of a BTK biomarker comprising or encoding a modification at a position corresponding position 316 of the sequence set forth in SEQ ID NO: 1; and (b) treating the subject with: (i) a BTK inhibitor if the subject does not exhibit the biomarker, or (ii) a non-BTK-inhibitor therapeutic is the subject exhibits the biomarker.

In some embodiments, the BTK biomarker is a nucleic acid (e.g., DNA, RNA, cDNA, etc.). In some embodiments, the nucleic acid is a cDNA. In some embodiments, the biomarker is detected using one or more reagents selected from oligonucleotide primers and/or probes.

In some embodiments, the BTK biomarker is a polypeptide. In some embodiments, the biomarker is detected using one or more reagents selected from antibodies, antibody fragments, and aptamers.

In some embodiments, the subject is administered a second generation BTK inhibitor that inhibits the modified BTK if the subject has the modification.

In some embodiments, methods further comprise administering an additional therapeutic or therapy for the treatment of cancer.

In some embodiments, methods further comprise obtaining the sample from the subject.

In some embodiments, the modification comprises a substitution, insertion, or a deletion of the amino acid at amino acid position 316 of a BTK polypeptide. In some embodiments, the modification is a substitution of threonine to an amino acid selected from the group consisting of leucine, isoleucine, valine, alanine, glycine, methionine, cysteine, serine, phenylalanine, tryptophan, lysine, arginine, histidine, proline, tyrosine, asparagine, glutamine, aspartic acid and glutamic acid at amino acid position 316 of the BTK polypeptide. In some embodiments, the substitution is a non-conservative and non-semi-conservative substitution. In some embodiments, the modification is a substitution of threonine to alanine at amino acid position 316 of the BTK polypeptide. In some embodiments, the modification comprises a deletion of the amino acid at position 316 of the BTK polypeptide. In some embodiments, the modification comprises an insertion at or spanning position 316 of the BTK polypeptide.

In some embodiments, the BTK inhibitor is reversible or irreversible. In some embodiments, the BTK inhibitor is selected from the group consisting of ibrutinib (PCI-32765), PCI-45292, PCI-45466, AVL-101, AVL-291, AVL-292, ONO-WG-37 Acalabrutinib, PRN-1008, GS-4059, BGB-3111, SNS-062, RDX-002, HCI-1401, TP-0158, GDC-0853, and ARQ 531. In some embodiments, the BTK inhibitor is ibrutinib.

In some embodiments, the subject has cancer. In some embodiments, the cancer is a hematologic cancer. In some embodiments, the cancer is a B-cell malignancy. In some embodiments, the cancer is selected from the group consisting of a leukemia, a lymphoma, or a myeloma. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor.

In some embodiments, the sample is obtained from the subject prior to initial administration of the BTK inhibitor. In some embodiments, the sample is a sample obtained between 1 week and 60 months (e.g., 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, 24 months, 30 months, 36 months, 42 months, 48 months, 54 months, 60 months, or ranges therebetween) following the initial administration of the BTK inhibitor. In some embodiments, the sample is obtained, and testing is performed, multiple times over the course of treatment with the BTK inhibitor. In some embodiments, the subject is responsive to treatment with the BTK inhibitor upon initial administration.

In some embodiments, provided herein is an isolated BTK polypeptide having BTK activity comprising a modification at a position corresponding to position 316 of the amino acid sequence set forth in SEQ ID NO: 1, wherein the modification confers resistance of the isolated BTK polypeptide to inhibition with a BTK inhibitor. In some embodiments, the modification comprises a substitution or a deletion of the amino acid at amino acid position 316 of a BTK polypeptide. In some embodiments, the modification is a substitution of threonine to an amino acid selected from the group consisting of leucine, isoleucine, valine, alanine, glycine, methionine, cysteine, serine, phenylalanine, tryptophan, lysine, arginine, histidine, proline, tyrosine, asparagine, glutamine, aspartic acid and glutamic acid at amino acid position 316 of the BTK polypeptide. In some embodiments, the substitution is a non-conservative and non-semi-conservative substitution. In some embodiments, the modification is a substitution of threonine to alanine at amino acid position 316 of the BTK polypeptide. In some embodiments, the modification comprises a deletion of nucleic acid encoding amino acid position 316 of the BTK polypeptide. In some embodiments, the polypeptide comprises one or more modifications relative to SEQ ID NO: 1. In some embodiments, the polypeptide comprises at least 70% (e.g., 70%, 75%, 80%, 85%, 90%, 95% 99%, or ranges therebetween) sequence identity with SEQ ID NO: 1. In some embodiments, the polypeptide comprises at least 70% (e.g., 70%, 75%, 80%, 85%, 90%, 95% 99%, or ranges therebetween) sequence similarity (e.g., conservative or semi-conservative) with SEQ ID NO: 1.

In some embodiments, provided herein are isolated nucleic acid molecules encoding a BTK polypeptide comprising at least 70% (e.g., 70%, 75%, 80%, 85%, 90%, 95% 99%, or ranges therebetween) sequence identity with SEQ ID NO: 1, and encoding a non-threonine amino acid at a position corresponding to position 316 or SEQ ID NO: 1. In some embodiments, provided herein are isolated nucleic acid molecules encoding a BTK polypeptide comprising at least 70% (e.g., 70%, 75%, 80%, 85%, 90%, 95% 99%, or ranges therebetween) sequence similarity (e.g., conservative or semi-conservative) with SEQ ID NO: 1, and encoding a non-threonine amino acid at a position corresponding to position 316 or SEQ ID NO: 1. In some embodiments, the nucleic acid is a DNA or an RNA molecule. In some embodiments, the nucleic acid is a cDNA. In some embodiments, the cDNA spans an exon-exon junction not present in the genomic BTK DNA. In some embodiments, the cDNA is at least 25 nucleotides. 50 nucleotides, 100 nucleotides, 150 nucleotides, 200 nucleotides, 250 nucleotides, 300 nucleotides, or more in length. In some embodiments, the cDNA is a full-length BTK cDNA. In some embodiments, a composition comprising a cDNA (e.g., BTK cDNA, BTK cDNA spanning an exon-exon junction, full-length BTK cDNA) is provided.

In some embodiments, provided herein are kits comprising one or more reagents for the detection of a mutant BTK polypeptide comprising a modification at position 316 or a nucleic acid encoding a mutant BTK polypeptide comprising a modification at amino acid position 316. In some embodiments, reagents comprise a pair oligonucleotide primers that flank the nucleic acid region encoding amino acid 361 of a BTK polypeptide. In some embodiments, reagents comprise a detectable oligonucleotide probe. In some embodiments, reagents comprise antibodies, antibody fragments, or aptamers.

The above embodiments, and additional embodiments are described in more detail in the Detailed Description, and exemplified in the Examples.

DEFINITIONS

Figure 1:
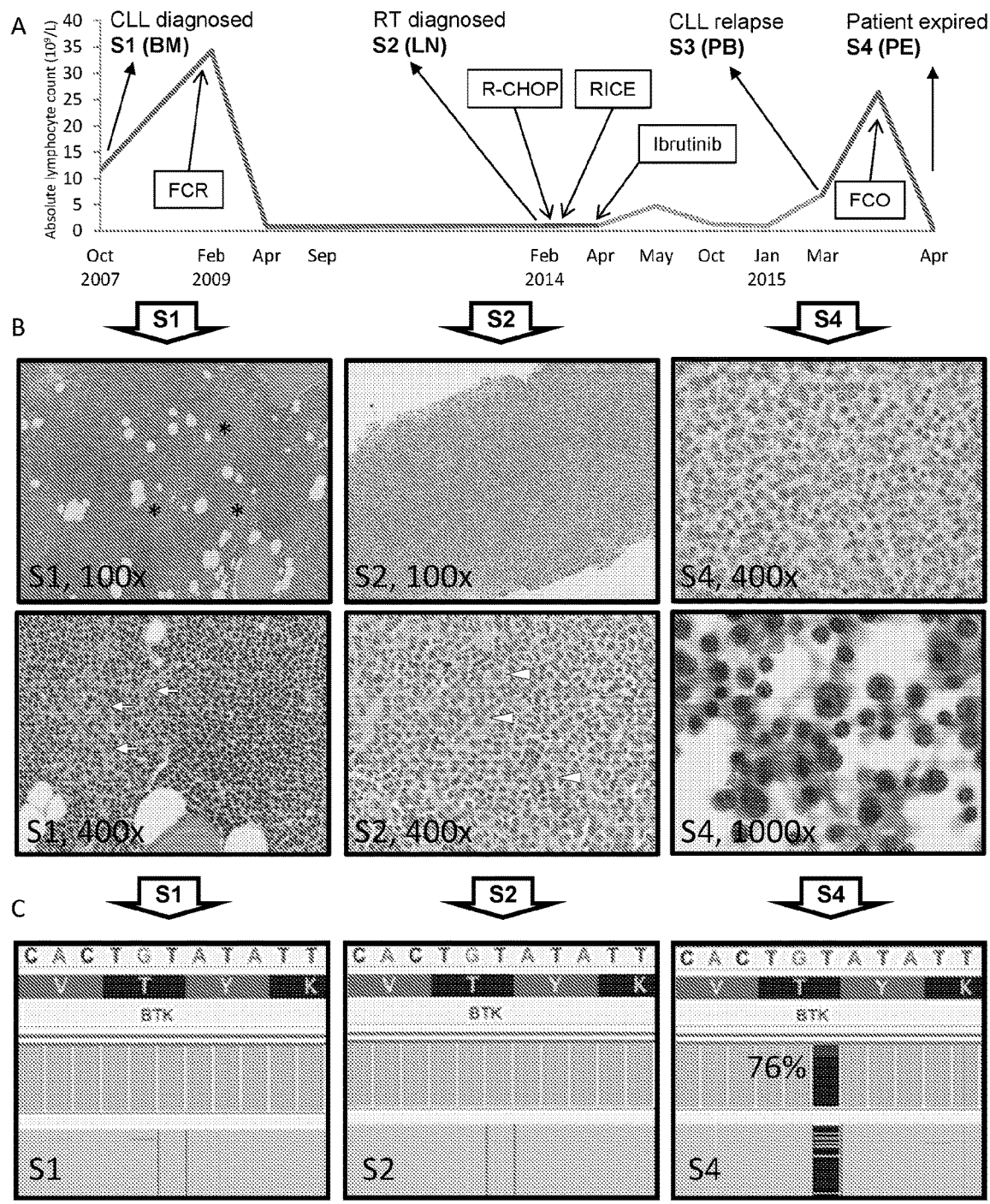
FIG. 1. Identification of BTK T316A mutation in the Richter-transformed and CLL-relapsed patient. (A) Patient's absolute lymphocytosis (ALC) is plotted over disease and treatment course. The four sample collection time points, S1-S4, are shown. BM, bone marrow; LN, lymph node; PB, peripheral blood; PE, pleural effusion. (B) Morphological progression of CLL to RT of large B-cell lymphoma. S1 (100×), bone marrow biopsy at the time of diagnosis shows hypercellular marrow extensively involved by CLL with an interstitial pattern; proliferation centers (black stars) can be seen as vaguely pale nodular areas at lower magnification. S1 (400×), higher magnification shows larger prolymphocytes (white arrows). There is no evidence of large cell transformation at this time. S2 (100×), lymph node core biopsy taken at the time of CLL progression. The lymph node architecture is effaced by a diffuse proliferation of CLL cells. S2 (400×), higher magnification shows mostly small cells with occasional large atypical lymphoid cells and mitotic figures (white arrowheads) not associated with proliferation centers. S4 (400×), cell block from pleural effusion collected shortly before patient expired. Numerous medium to large lymphoid cells are present. S4 (1000×), higher magnification shows highly atypical cells with frequent mitotic figures consistent with Richter transformation to large B-cell lymphoma. (C) Integrative Genomics Viewer (IGV) profile of $BTK^{T316A}$ mutation of the 3 samples. Data presented are results sequenced using the CLL panel.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a BTK mutation" is a reference to one or more BTK mutations and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "subject at risk for a disease," for example, "a subject at risk for cancer" refers to a subject with one or more risk factors for developing the disease (e.g., cancer). Depending upon the specific disease, risk factors may include, but are not limited to, gender, age, genetic predisposition, environmental exposures, infections, and previous incidents of diseases, lifestyle, etc.

"Biological sample", "sample", and "test sample" are used herein to refer to any material, biological fluid, tissue, or cell obtained or otherwise derived from a subject. This includes blood (e.g., whole blood, leukocytes, peripheral blood mononuclear cells, buffy coat, plasma, and serum), sputum, tears, mucus, nasal washes, nasal aspirate, urine, semen, saliva, peritoneal washings, ascites, cystic fluid, meningeal fluid, amniotic fluid, glandular fluid, lymph fluid, nipple aspirate, bronchial aspirate (e.g., bronchoalveolar lavage), bronchial brushing, synovial fluid, joint aspirate, organ secretions, cells, a cellular extract, and cerebrospinal fluid. This also includes experimentally separated fractions of all of the receding. For example, a blood sample can be fractionated into serum, plasma, or into fractions containing particular types of blood cells, such as red blood cells or white blood cells (leukocytes). In some embodiments, a sample can be a combination of samples from an individual, such as a combination of a tissue and fluid sample. The term "sample" may also include materials containing homogenized solid material, such as from a stool sample, a tissue sample, or a tissue biopsy; and materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Exemplary tissues susceptible to fine needle aspiration include lymph node, lung, lung washes, BAL (bronchoalveolar lavage), thyroid, breast, pancreas, and liver. Samples can also be collected, e.g., by micro dissection (e.g., laser capture micro dissection (LCM) or laser micro dissection (LMD)), bladder wash, smear (e.g., a PAP smear), or ductal lavage. A sample obtained or derived from an individual includes any such sample that has been processed in any suitable manner (e.g., filtered, diluted, pooled, fractionated, concentrated, etc.) after being obtained from the individual.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., BTK inhibitor and one or more additional therapeutics) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "mutant" refers to a variant of a polypeptide or nucleic acid having a distinct amino acid sequence from the most common variant occurring in nature, referred to as the "wild-type" sequence. A mutant may be a naturally-occurring polypeptide or nucleic acid that is not the most common variant of that sequence found in nature, or may be a polypeptide or nucleic acid that is not a naturally-occurring polypeptide or nucleic acid.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

"Non-conservative substitutions" involve the exchange of a member of one of the above groups for a member from another group (i.e., not conservative).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class. "Non-semi-conservative substitutions" involve the exchange of a member of one of the above classes for a member from another class (i.e., not semi-conservative).

As used herein, the term "sequence identity" refers to the degree to which two polymer sequences (e.g., polypeptide, nucleic acid, etc.) have the same sequential composition of monomer subunits. The term "sequence similarity" refers to the degree with which two polymer sequences (e.g polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, a "capture agent" or "capture reagent" refers to a molecule that binds specifically to a biomarker or target molecule (e.g., a polynucleotide or nucleic acid). A "target protein capture reagent" refers to a molecule that binds specifically to a target protein. A "target nucleic acid capture reagent" refers to a molecule that binds specifically to a target protein. Nonlimiting exemplary capture reagents include aptamers, antibodies, adnectins, ankyrins, other antibody mimetics and other protein scaffolds, autoantibodies, chimeras, small molecules, nucleic acids (e.g., probes), lectins, ligand-binding receptors, imprinted polymers, avimers, peptidomimetics, hormone receptors, cytokine receptors, synthetic receptors, and modifications and fragments of any of the aforementioned capture reagents.

The term "antibody" refers to full-length antibodies of any species and fragments and derivatives of such antibodies, including Fab fragments, F(ab')2 fragments, single chain antibodies, Fv fragments, and single chain Fv fragments. The term "antibody" also refers to synthetically-derived antibodies, such as phage display-derived antibodies and fragments, affybodies, nanobodies, etc.

The term "nucleic acid probe" or "probe" refers to a molecule capable of sequence specific hybridization to a nucleic acid, and includes analogs of nucleic acids, as are known in the art, e.g. DNA, RNA, peptide nucleic acids, and the like, and may be double-stranded or single-stranded. Also included are synthetic molecules that mimic nucleic acid molecules in the ability to bind to a designated sequence via hydrogen bonding and other chemical interactions. Such molecules include, for example, those in which peptide linkages substitute for phosphate linkages in the backbone of the molecule.

As used herein, "marker" and "biomarker" are used interchangeably to refer to a target molecule that indicates or is a sign of a normal or abnormal process in an individual or of a disease or other condition in an individual. More specifically, a "marker" or "biomarker" is an anatomic, physiologic, biochemical, or molecular parameter associated with the presence of a specific physiological state or process, whether normal or abnormal, and, if abnormal, whether chronic or acute. Biomarkers are detectable and measurable by a variety of methods including laboratory assays and medical imaging. In some embodiments, a biomarker is a target protein (e.g., BTK (e.g. modified BTK)). In some embodiments, a biomarker is a target nucleic acid (e.g., a BTK nucleic acid (e.g., a nucleic acid encoding a modified BTK)).

As used herein, "biomarker level" and "level" refer to a measurement that is made using any analytical method for detecting the biomarker in a biological sample and that indicates the presence, absence, absolute amount or concentration, relative amount or concentration, titer, a level, an expression level, a ratio of measured levels, or the like, of, for, or corresponding to the biomarker in the biological sample. The exact nature of the "level" depends on the specific design and components of the particular analytical method employed to detect the biomarker.

A "control level" of a target molecule refers to the level of the target molecule in the same sample type from an individual that does not have the disease or condition. A "control level" of a target molecule need not be determined each time the present methods are carried out, and may be a previously determined level that is used as a reference or threshold to determine whether the level in a particular sample is higher or lower than a normal level. In some embodiments, a control level in a method described herein is the level that has been observed in one or more control subjects (e.g., subjects that are responsive to treatment with BTK inhibitors). In some embodiments, a control level in a method described herein is the average or mean level, optionally plus or minus a statistical variation that has been observed in a plurality of control subjects (e.g., subjects that are responsive to treatment with BTK inhibitors).

A "threshold level" of a target molecule refers to the level beyond which (e.g., above or below, depending upon the biomarker) is indicative of or diagnostic for a particular disease or condition (e.g., resistance to treatment with a BTK inhibitor, risk of developing resistance to treatment with a BTK inhibitor, etc.). A "threshold level" of a target molecule need not be determined each time the present methods are carried out, and may be a previously determined level that is used as a reference or threshold to determine whether the level in a particular sample is higher or lower than a normal level. In some embodiments, a subject with a biomarker level beyond (e.g., above or below, depending upon the biomarker) a threshold level has a statistically significant likelihood (e.g., 80% confidence, 85% confidence, 90% confidence, 95% confidence, 98% confidence, 99% confidence, 99.9% confidence, etc.) of, for example, having or developing resistance to treatment with BTK inhibitors.

"Diagnose", "diagnosing", "diagnosis", and variations thereof refer to the detection, determination, or recognition of a health status or condition of an individual on the basis of one or more signs, symptoms, data, or other information pertaining to that individual. The health status of an individual can be diagnosed as healthy/normal (e.g., a diagnosis of the absence of a disease or condition) or diagnosed as ill/abnormal (e.g., a diagnosis of the presence, or an assessment of the characteristics, of a disease or condition). The terms "diagnose", "diagnosing", "diagnosis", etc., encompass, with respect to a particular disease or condition, the initial detection of the disease; the characterization or classification of the disease; the detection of the progression, remission, or recurrence of the disease; and the detection of disease response after the administration of a treatment or therapy to the individual.

"Prognose", "prognosing", "prognosis", and variations thereof refer to the prediction of a future course of a disease or condition in an individual who has the disease or condition (e.g., predicting patient survival, predicting the need for organ transplant, etc.), and such terms encompass the evaluation of disease response after the administration of a treatment or therapy to the individual. Example prognoses include likelihood of mortality (e.g., <1%, <5%, <10<, <20%, <30%, <40%, <50%, >50%, >60%, >70%, >80%, >90%, >95%, >99%), likelihood of responsiveness/resistance to treatment (e.g., <1%, <5%, <10<, <20%, <30%, <40%, <50%, >50%, >60%, >70%, >80%, >90%, >95%, >99%), likely lifespan (e.g., <1 month, <2 months, <3 month, <6 months, <1 year, 2 years, 3 years, >3 years, etc.).

"Evaluate", "evaluating", "evaluation", and variations thereof encompass both "diagnosis" and "prognosis" and also encompass determinations or predictions about the future course of a disease or condition in an individual who does not have the disease as well as determinations or predictions regarding the likelihood that a disease or condition will recur in an individual who apparently has been cured of the disease. The term "evaluate" also encompasses assessing an individual's response to a therapy, such as, for example, predicting whether an individual is likely to respond favorably to a therapeutic agent (e.g., a BTK inhibitor) or is likely to develop resistance to a therapeutic agent (a BTK inhibitor), selecting a therapeutic agent for administration to an individual, or monitoring or determining an individual's response to a therapy that has been administered to the individual.

As used herein, "detecting" or "determining" with respect to a biomarker (e.g., BTK polypeptide or nucleic acid) includes the use of both the instrument used (if used) to observe and record a signal corresponding to a biomarker and the reagents required to generate that signal. In various embodiments, the level is detected using any suitable method, including fluorescence, chemiluminescence, surface plasmon resonance, surface acoustic waves, mass spectrometry, infrared spectroscopy, Raman spectroscopy, atomic force microscopy, scanning tunneling microscopy, electrochemical or biochemical detection methods, nuclear magnetic resonance, quantum dots, and the like.

"Solid support" refers herein to any substrate having a surface to which molecules may be attached, directly or indirectly, through either covalent or non-covalent bonds. A "solid support" can have a variety of physical formats, which can include, for example, a membrane; a chip (e.g., a protein chip); a slide (e.g., a glass slide or coverslip); a column; a hollow, solid, semi-solid, pore- or cavity-containing particle, such as, for example, a bead; a gel; a fiber, including a fiber optic material; a matrix; and a sample receptacle. Exemplary sample receptacles include sample wells, tubes, capillaries, vials, and any other vessel, groove or indentation capable of holding a sample. A sample receptacle can be contained on a multi-sample platform, such as a microtiter plate, slide, microfluidics device, and the like. A support can be composed of a natural or synthetic material, an organic or inorganic material. The composition of the solid support on which capture reagents are attached generally depends on the method of attachment (e.g., covalent attachment). Other exemplary receptacles include microdroplets and microfluidic controlled or bulk oil/aqueous emulsions within which assays and related manipulations can occur. Suitable solid supports include, for example, plastics, resins, polysaccharides, silica or silica-based materials, functionalized glass, modified silicon, carbon, metals, inorganic glasses, membranes, nylon, natural fibers (such as, for example, silk, wool and cotton), polymers, and the like. The material composing the solid support can include reactive groups such as, for example, carboxy, amino, or hydroxyl groups, which are used for attachment of the capture reagents. Polymeric solid supports can include, e.g., polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly)vinylidenefluoride, polycarbonate, and polymethylpentene. Suitable solid support particles that can be used include, e.g., encoded particles, such as Luminex®-type encoded particles, magnetic particles, and glass particles.

DETAILED DESCRIPTION

Provided herein are mutations in Bruton's Tyrosine Kinase (BTK) that confer resistance to treatment with BTK inhibitors, such as Ibrutinib, and compositions and methods for the treatment, diagnosis, and characterization of BTK-inhibitor-resistant cancers.

Experiments conducted during development of embodiments herein identified a patient whose disease progressed, was salvaged with ibrutinib and relapsed with Richter transformation. Serial analysis of samples throughout patient's clinical course identified a structurally novel mutation ($BTK^{T316A}$) in the SH2 domain, but not kinase domain, of Bruton tyrosine kinase which was associated with CLL relapse but not Richter transformation. Functionally, cells carrying $BTK^{T316A}$ show resistance to ibrutinib at both cellular and molecular levels to a similar extent as $BTK^{C481S}$. Unlike other BTK kinase domain mutations (C481S, T474A, and L528W) that may confer drug resistance through either attenuating or directly inhibiting ibr binding, T316A is located in the SH2 domain, distant from the drug binding site. Functional studies at both cellular and molecular levels demonstrate that T316A confers ibr resistance to a similar extent as C481S.

In some embodiments, provided herein is the identification, detection, and/or characterization of mutations in the B-cell receptor pathway that confer resistance of patients to treatment with a BTK inhibitor. In some embodiments, the BTK inhibitor covalently binds to BTK. In some embodiments, the BTK inhibitor non-associates with BTK. In some embodiments, the BTK inhibitor binds the kinase domain of BTK. In some embodiments, the BTK inhibitor binds the ATP binding domain of BTK. In some embodiments, the BTK inhibitor binds to Cysteine 481 of BTK. In some embodiments, the BTK inhibitor is ibrutinib.

In some embodiments, the methods, compositions, kits, etc. provided herein find use in making a determination regarding therapy continuation, therapy discontinuation, therapy selection, therapy optimization, etc. In some embodiments, the methods herein allow a clinician and/or subject to determine where a subject is resistant to treatment with certain BTK inhibitors, is likely to become resistant to certain BTK inhibitors, etc., and to make the aforementioned therapy decisions.

In some embodiments, a subject (e.g., patient) treated and/or analyzed in embodiments herein has, is suspected of having, or is at risk for a B-cell proliferative disorder. In some embodiments, the subject has, is suspected of having, or is at risk for a B-cell malignancy. In some embodiments, the subject has, is suspected of having, or is at risk for a leukemia or a lymphoma. In some embodiments, the subject has, is suspected of having, or is at risk for Non-Hodgkin's Lymphoma. In some embodiments, the subject has, is suspected of having, or is at risk for chronic lymphocytic leukemia (CLL), mantle cell leukemia (MCL), follicular lymphoma (FL), diffuse large B-cell lymphoma (DLBCL), or multiple myeloma (MM). In some embodiments, the subject has, is suspected of having, or is at risk for a solid tumor, such as a carcinoma or a sarcoma.

Described herein are mutations in BTK that confer resistance of BTK to inhibition by BTK inhibitors, for example, inhibitors that bind (e.g., covalently, non-covalently, etc.) to BTK (e.g., to the kinase domain (e.g., to Cysteine 481, etc.), etc.) and prevent its activity. In some embodiments, isolated mutant BTK polypeptides and isolated nucleic acids encoding mutant BTK polypeptides are provided. In some embodiments, identification/detection/characterization of the mutations described herein (or the absence thereof) allows for appropriate therapeutic regimes (e.g., administer ibrutinib, co-administer ibrutinib with one or more additional therapeutics/therapies, do not administer ibrutinib, administer non-ibrutinib therapeutics/therapies, etc.) to be selected for a subject. In some embodiments, identification/detection/characterization of the mutations described herein allows for the selection of patients for BTK-inhibitor therapy, monitoring patients receiving BTK-inhibitor therapy, and/or modification of BTK-inhibitor therapeutic regimens. In some embodiments, described herein are diagnostic methods for detecting mutant BTK polypeptides and nucleic acids encoding mutant BTK polypeptides and therapeutic uses of such methods. Also described herein are methods for the identification of new BTK inhibitors that inhibit the mutant BTK polypeptides.

In some embodiments, the compositions and methods described herein relate to the treatment, diagnosis, and characterization of cancers such as acute myeloid leukemia, cancer in adolescents, adrenocortical carcinoma childhood, AIDS-related cancers, e.g., Lymphoma and Kaposi's Sarcoma, anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, the method relates to the treatment of a non-cancerous hyperproliferative disorder such as benign hyperplasia of the skin, e.g., psoriasis, restenosis, or prostate, e.g., benign prostatic hypertrophy (BPH). In some cases, the method relates to the treatment of leukemia, hematologic malignancy, solid tumor cancer, prostate cancer, e.g., castration-resistant prostate cancer, breast cancer, Ewing's sarcoma, bone sarcoma, primary bone sarcoma, T-cell prolymphocyte leukemia, glioma, glioblastoma, liver cancer, e.g., hepatocellular carcinoma, or diabetes.

In some embodiments herein, subject being treated and/or analyzed has cancer. In some embodiments, the cancer is a hematologic cancer. In some embodiments, cancer is a B-cell malignancy. In some embodiments, cancer is selected from the group consisting of a leukemia, a lymphoma, or a myeloma. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor.

In some embodiments, the compositions and methods described herein relate to the treatment, diagnosis, and characterization of B-cell malignancies, including, but not limited to Non-Hodgkin's Lymphomas, such as chronic lymphocytic leukemia (CLL), mantle cell leukemia (MCL), follicular lymphoma (FL) and diffuse large B-cell lymphoma (DLBCL), and multiple myeloma (MM).

In some embodiments, provided herein are mutant BTK polypeptides and nucleic acids comprising modifications (e.g., substitutions, deletions, insertions, etc.) that confer resistance to treatment with BTK inhibitors. In some embodiments, the modification is in the SH2 domain of BTK. In some embodiments, the modification comprises a substitution, insertion, or a deletion of the amino acid at amino acid position 316 in the BTK polypeptide. In some embodiments, the modification comprises substitution, insertion, or deletion of amino acids spanning position 316 in the BTK polypeptide. In some embodiments, the modification is a substitution of the threonine at position 316 of BTK to an amino acid selected from leucine, isoleucine, valine, alanine, glycine, cysteine, methionine, serine, phenylalanine, tryptophan, lysine, arginine, histidine, proline, tyrosine, asparagine, glutamine, aspartic acid and glutamic acid. In some embodiments, the modification is a non-conservative substation of the threonine at position 316 of BTK to an amino acid selected from leucine, isoleucine, valine, alanine, glycine, cysteine, methionine, phenylalanine, tryptophan, lysine, arginine, histidine, proline, tyrosine, asparagine, glutamine, aspartic acid and glutamic acid. In some embodiments, the modification is a non-semi-conservative substation of the threonine at position 316 of BTK to an amino acid selected from histidine, lysine, and arginine, aspartic acid, glutamic acid, alanine, valine, leucine, isoleucine, methionine, phenylalanine, tyrosine, tryptophan, proline, glycine, and cysteine. In some embodiments, the modification is a substitution of threonine to alanine at amino acid position 316 of the BTK. In some embodiments, a mutant BTK nucleic acid is provided that encodes one or the aforementioned BTK mutant polypeptides (e.g., one having a mutation at position 316).

In some embodiments, mutation of other (e.g., non-316) SH2-domain positions in BTK confers similar resistance and/or risk of developing resistance to BTK inhibitors as modification of position 316. Polypeptides comprising such mutations (e.g., alone or in addition to mutation at position 316) and nucleic acids encoding such polypeptides are within the scope herein.

In some embodiments, a mutant polypeptide comprises additional BTK-inhibitor resistance mutations in the SH2 domain (e.g., in addition to the substitution or deletion at position 316 of BTK), polypeptides herein (and nucleic acids encoding such polypeptides) additionally comprise mutations (e.g., substitution, deletion, etc.) at other positions within BTK. In some embodiments, additional mutation are within the kinase domain of BTK. For example, a mutant BTK polypeptide may comprise mutations at one or more of positions 481 (e.g., C481 to another amino acid (e.g., S)), 474 (e.g., T474 to another amino acid (e.g., A)), 528 (e.g., L528 to another amino acid (e.g., W)), etc.

In some embodiments, a subject is being treated with a BTK inhibitor, has been treated with a BTK inhibitor, and/or is a candidate for treatment with a BTK inhibitor. In some embodiments of the methods, the BTK inhibitor is a non-covalent BTK inhibitor In some embodiments of the methods, the BTK inhibitor is a covalent and/or irreversible BTK inhibitor, for example, an agent that covalently binds to cysteine 481 of BTK. In some embodiments, the BTK inhibitor is reversible or irreversible. In some embodiments, the BTK inhibitor is selected from the group consisting of ibrutinib (PCI-32765), PCI-45292, PCI-45466, AVL-101, AVL-291, AVL-292, ONO-WG-37 Acalabrutinib, PRN-1008, GS-4059, BGB-3111, SNS-062, RDX-002, HCI-1401, TP-0158, GDC-0853, and ARQ 531.

In some embodiments, the BTK inhibitor is ibrutinib. In some embodiments, ibrutinib is a first generation BTK inhibitors. In some embodiments, a second generation BTK inhibitor is an agent that evades resistance to first generation BTK inhibitors caused by a mutation of BTK (e.g., at position 316).

In some embodiments, analysis of a subject (e.g., of a sample from the subject) is conducted in advance of treatment with a BTK inhibitor. In some embodiments, the subject is treated with the BTK inhibitor prior to obtaining the sample. In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, 24 months, 30 months, 36 months, 42 months, 48 months, 54 months, or 60 months (or ranges therebetween) following the first administration of the BTK inhibitor. In some embodiments, the sample is obtained multiple times (e.g., 1, 2, 3, 4, 5, 6, 7, 8, 9, 10, or more times (or ranges therebetween)) over the course of treatment with the BTK inhibitor. In some embodiments, the subject is responsive the treatment with the irreversible BTK inhibitor upon initial administration.

In some embodiments, methods comprise detecting and/or quantifying mutant BTK polypeptides (e.g., BTK harboring a modification at position 316) and/or nucleic acids encoding such polypeptides in a sample from a subject. In some embodiments, methods comprise contacting a sample or a portion of a sample from a subject with at least one detection/capture reagent, wherein each capture reagent specifically binds the BTK biomarker (e.g., polypeptide, nucleic acid, etc.), and the presence and/or level of the BTK biomarker is detected. In some embodiments, capture reagents are antibodies, aptamers, nucleic acid probes, primers, etc.

In addition to analyzing BTK as a stand-alone diagnostic/prognostic test, in some embodiments, BTK biomarkers are tested in conjunction with other markers or assays that are indicative of a particular aspects of a cancer diagnosis/prognosis/evaluation. BTK biomarkers may also be evaluated in conjunction with other types of data, particularly data that indicates a subject's prognosis (e.g., lifestyle, genetics, age, etc.). These various data can be assessed by automated methods, such as a computer program/software, which can be embodied in a computer or other apparatus/device within the scope herein.

In certain embodiments, provided herein are methods for determining whether a subject is likely to heroine resistant to treatment with a BTK inhibitor (e.g., covalent BTK inhibitor or non-covalent BTK inhibitor), comprising testing a sample from the subject containing a nucleic acid molecule encoding a BTK polypeptide to determine whether the encoded BTK polypeptide is modified at an amino acid position corresponding to amino acid position 316 of the amino acid sequence set forth in SEQ ID NO: 1; and characterizing the subject as likely to become resistant to treatment with a BTK inhibitor if the nucleic acid exhibits the modification at position 316.

In certain embodiments, provided herein are methods fir determining whether a subject is likely to become resistant to treatment with a BTK inhibitor (e.g., covalent BTK inhibitor or non-covalent BTK inhibitor), comprising testing a sample from the subject containing a BTK polypeptide to determine whether the BTK polypeptide is modified at an amino acid position corresponding to amino acid position 316 of the amino acid sequence set forth in SEQ ID NO: 1; and characterizing the subject as likely to become resistant to treatment with a BTK inhibitor if the BTK polypeptide exhibits the modification at position 316.

In some embodiments, provided herein are methods for characterizing a BTK polypeptide as resistant to inhibition with a BTK inhibitor, comprising testing a sample containing a nucleic acid molecule encoding the BTK polypeptide to determine whether the encoded BTK polypeptide is modified at an amino acid position corresponding to position 316 of the amino acid sequence set forth in SEQ ID NO: 1; and characterizing BTK as resistant to inhibition with a BTK inhibitor if the modification is present.

In some embodiments, provided herein are methods for characterizing a BTK polypeptide as resistant to inhibition with a BTK inhibitor, comprising testing a sample containing the BTK polypeptide to determine whether the BTK polypeptide is modified at an amino acid position corresponding to position 316 of the amino acid sequence set forth in SEQ ID NO: 1; and characterizing BTK as resistant to inhibition with a BTK inhibitor if the modification is present.

In certain embodiments herein are methods for monitoring whether a subject receiving a BTK inhibitor for treatment of a cancer has developed or is likely to develop resistance to the therapy, comprising testing a sample containing a nucleic acid molecule encoding a BTK polypeptide from the subject to determine whether the encoded BTK polypeptide is modified at a position corresponding to amino acid position 316 of the amino acid sequence set forth in SEQ ID NO: 1; and characterizing the subject as resistant or is likely to become resistant to therapy with the BTK inhibitor if the subject has the modification. In some embodiments, the method further comprises discontinuing treatment with the BTK inhibitor if the subject has the modification. In some embodiments, the method further comprises continuing treatment with a BTK inhibitor if the subject does not have the modification. In some embodiments, the method further comprises administering second generation BTK inhibitor that inhibits the modified kinase if the subject has the modification. In some embodiments, the method further comprises administering a different cancer treatment (e.g., other than BTK inhibition) if the subject has the modification. In some embodiments, the method further comprises administering an inhibitor of BTK that is not affected by modifications at position 316 if the subject has the modification.

In certain embodiments are methods for monitoring whether a subject receiving a BTK inhibitor for treatment of a cancer has developed or is likely to develop resistance to the therapy, comprising testing a sample containing a BTK polypeptide from the subject to determine whether the BTK polypeptide is modified at a position corresponding to amino acid position 316 of the amino acid sequence set forth in SEQ ID NO: 1, and characterizing the subject as resistant or is likely to become resistant to therapy with the BTK inhibitor if the subject has the modification. In some embodiments, the method further comprises discontinuing treatment with the BTK inhibitor if the subject has the modification. In some embodiments, the method further comprises continuing treatment with a BTK inhibitor if the subject does not have the modification. In some embodiments, the method further comprises administering second generation BTK inhibitor that inhibits the modified kinase if the subject has the modification. In some embodiments, the method further comprises administering a different cancer treatment (e.g., other than BTK inhibition) if the subject has the modification. In some embodiments, the method further comprises administering an inhibitor of BTK that is not affected by modifications at position 316 if the subject has the modification.

In certain embodiments herein are methods for optimizing the therapy of a subject receiving a BTK inhibitor for treatment of a cancer, comprising testing s sample containing a nucleic acid molecule encoding a BTK polypeptide from the subject to determine whether the encoded BTK polypeptide is modified at a position corresponding to position 316 of the amino acid sequence set forth in SEQ ID NO: 1; and discontinuing treatment with the BTK inhibitor if the subject has the modification or continuing treatment with the BTK inhibitor if the subject does not have the modification. In some embodiments, the method further comprises administering second generation BTK inhibitor that inhibits the modified kinase if the subject has the modification. In some embodiments, the method further comprises administering a different cancer treatment (e.g., other than BTK inhibition) if the subject has the modification. In some embodiments, the method further comprises administering an inhibitor of BTK that is not affected by modifications at position 316 if the subject has the modification.

In certain embodiments herein are methods for optimizing the therapy of a subject receiving a BTK inhibitor for treatment of a cancer, comprising testing s sample containing a. BTK polypeptide from the subject to determine whether the BTK polypeptide is modified at a position corresponding to position 316 of the amino acid sequence set forth in SEQ ID NO: 1; and discontinuing treatment with the BTK inhibitor if the subject has the modification or continuing treatment with the BTK inhibitor if the subject does not have the modification. In some embodiments, the method further comprises administering second generation BTK inhibitor that inhibits the modified kinase if the subject has the modification. In some embodiments, the method further comprises administering a different cancer treatment (e.g., other than BTK inhibition) if the subject has the modification. In some embodiments, the method further comprises administering an inhibitor of BTK that is not affected by modifications at position 316 if the subject has the modification.

In some embodiments, methods are provided comprising generating a mutation in a BTK polypeptide or nucleic acid encoding a BTK polypeptide, wherein the mutation is at a position corresponding to position 316 of the amino acid sequence set forth in SEQ ID NO: 1; detecting the presence of the mutation; and altering a treatment course of action for a subject based on the presence of the mutation. In some embodiments, generating the mutation comprises administering a BTK inhibitor to a subject. In some embodiments, altering the treatment course of action comprises ceasing treatment of the subject with a BTK inhibitor. In some embodiments, the BTK inhibitor is ibrutinib. In some embodiments, the presence of the mutation is monitored over the course of treatment with the BTK inhibitor.

In some embodiments, methods are provided comprising detecting the presence or absence of a low-abundance mutation in a nucleic acid encoding a BTK polypeptide in a sample from a subject, wherein the mutation is at a position corresponding to position 316 of the amino acid sequence set forth in SEQ ID NO: 1, and wherein the subject suffers from a cancer; initiating treatment of the subject with a BTK inhibitor if the mutation is not detected in the sample. In some embodiments, low-abundance mutations are detected by deep targeted sequencing of BTK. In some embodiments, a low-abundance mutation is present in >10%, >5%, <4%, <3%, <2%, <1%, <0.5%, <0.1% of nucleic acids in the sample. In some embodiments, if the mutation at positon 316 is identified, a treatment or therapy other than administration of a BTK inhibitor is pursued (e.g., allogeneic transplantation).

Provided herein, in certain embodiments are methods for selecting a subject for therapy with a second generation BTK inhibitor, comprising testing a sample from the subject containing a nucleic acid molecule encoding a BTK polypeptide to determine whether the encoded BTK polypeptide is modified at a position corresponding to position 316 of the amino acid sequence set forth in SEQ ID NO: 1; and characterizing the subject as a candidate for therapy with a second generation BTK inhibitor if the subject has the modification. In some embodiments, the method further comprises administering second generation BTK inhibitor that inhibits the mutant BTK if the subject has the modification.

Provided herein, in certain embodiments are methods for selecting a subject for therapy with a second generation BTK inhibitor, comprising testing a sample from the subject containing a BTK polypeptide to determine whether the BTK polypeptide is modified at a position corresponding to position 316 of the amino acid sequence set forth in SEQ ID NO: 1; and characterizing the subject as a candidate for therapy with a second generation BTK inhibitor if the subject has the modification. In some embodiments, the method further comprises administering second generation BTK inhibitor that inhibits the mutant BTK if the subject has the modification.

In some embodiments of the methods, the biological material (e.g., polypeptides, nucleic acid, etc.) analyzed in the methods herein is obtained and/or isolated from a tumor biopsy sample, a blood sample, a serum sample, a lymph sample, a bone marrow aspirate, etc.

BTK polypeptides and nucleic acids (e.g., mutant BTK harboring a modification at position 316) described herein can be detected/quantified using any of a variety of analytical methods. In one embodiment, BTK biomarker polypeptide, nucleic acid) presence/level is detected using a capture reagent. In various embodiments, the capture reagent is exposed to the BTK biomarker in solution or is exposed to the BTK biomarker while the capture reagent is immobilized on a solid support. In other embodiments, the capture reagent contains a feature that is reactive with a secondary feature on a solid support. In these embodiments, the capture reagent is exposed to the BTK biomarker in solution, and then the feature on the capture reagent is used in conjunction with the secondary feature on the solid support to immobilize the biomarker on the solid support. The capture reagent is selected based on the type of analysis to be conducted. Capture reagents include but are not limited to aptamers, antibodies, adnectins, ankyrins, other antibody mimetics and other protein scaffolds, autoantibodies, chimeras, small molecules, F(ab')2 fragments, single chain antibody fragments, Fv fragments, single chain Fv fragments, nucleic acids, lectins, ligand-binding receptors, affybodies, nanobodies, imprinted polymers, avimers, peptidomimetics, hormone receptors, cytokine receptors, and synthetic receptors, and modifications and fragments of these.

In some embodiments, BTK biomarkers (e.g., polypeptide, nucleic acid) are detected using a multiplexed format that allows for the simultaneous detection of BTK biomarkers (e.g., substitution at position 316) with other biomarkers (e.g., BTK substitutions at other positions, non-BTK biomarkers, etc.) in a biological sample. In some embodiments of the multiplexed format, capture reagents are immobilized, directly or indirectly, covalently or non-covalently, in discrete locations on a solid support. In some embodiments, a multiplexed format uses discrete solid supports where each solid support has a unique capture reagent associated with that solid support. In some embodiments, an individual device is used for the detection of each one of multiple biomarkers to be detected in a biological sample. Individual devices are configured to permit each biomarker in the biological sample to be processed simultaneously. For example, a microtiter plate can be used such that each well in the plate is used to analyze one or more of multiple biomarkers to be detected in a biological sample.

In certain embodiments, a fluorescent tag is used to label a component of a BTK-biomarker/capture reagent complex to enable the detection of the BTK biomarker presence/level. In various embodiments, the fluorescent label is conjugated to a capture reagent using known techniques, and the fluorescent label is then used to detect the corresponding BTK biomarker level. Suitable fluorescent labels include rare earth chelates, fluorescein and its derivatives, rhodamine and its derivatives, dansyl, allophycocyanin, PBXL-3, Qdot 605, Lissamine, phycoerythrin, Texas Red, and other such compounds. In some embodiments, the fluorescent label is a fluorescent dye molecule. Fluorescence can be measured with a variety of instrumentation compatible with a wide range of assay formats. For example, spectrofluorimeters have been designed to analyze microtiter plates, microscope slides, printed arrays, cuvettes, etc. See Principles of Fluorescence Spectroscopy, by J. R. Lakowicz, Springer Science+Business Media, Inc., 2004. See Bioluminescence & Chemiluminescence: Progress Current Applications; Philip E. Stanley and Larry J. Kricka editors, World Scientific Publishing Company, January 2002.

In one or more embodiments, a chemiluminescence tag is optionally used to label a component of the BTK-biomarker/capture complex to enable the detection of BTK biomarker presence/level. Suitable chemiluminescent materials include any of oxalyl chloride, Rodamin 6G, Ru(bipy)32+, TMAE (tetrakis(dimethylamino)ethylene), Pyrogallol (1,2,3-trihydroxibenzene), Lucigenin, peroxyoxalates, Aryl oxalates, Acridinium esters, dioxetanes, and others.

Certain embodiments herein comprise the detection of a BTK nucleic acid (e.g., a nucleic acid encoding BTK (e.g., BTK harboring a non-wild-type amino acid at position 316)). In some embodiments of the methods, the nucleic acid molecule for use in the assay is RNA or DNA. In some embodiments of the methods, the nucleic acid molecule for use in the assay is genomic DNA. In some embodiments of the methods, the nucleic acid molecule for use in the assay is total RNA, In some embodiments of the methods, the nucleic acid molecule for use in the assay is mRNA. In some embodiments of the methods, the method further comprises isolating mRNA from the RNA sample. In some embodiments, the assays described herein analyze genomic DNA, circulating tumor DNA, RNA, mRNA and its derivative cDNA In some embodiments, a BTK nucleic acid may be detected by PCR-based, nucleic acid probe-based, and/or sequencing-based detection techniques.

In some embodiments, oligonucleotide primers are provided for amplification of a region of a BTK nucleic acid encompassing a portion that encodes a BTK kinase and/or SH2 domain. In some embodiments, primers and/or probes (e.g., with detectable labels) are provided that hybridize to BTK nucleic acids encoding a polypeptide having a substitution in the kinase and/or SH2 domain, but not to wild-type. In some embodiments, primers and/or probes (e.g., with detectable labels) are provided that hybridize to wild-type BTK nucleic acids but not to those having a modification in the kinase and/or SH2 domain. In some embodiments, a primer or probe binds to a portion of a nucleic acid encoding a polypeptide comprising a modification in the SH2 or kinase domain or a region flanking sucha modification (e.g., within 100 bases, within 75 bases, within 50 bases, within 25 bases, within 20 bases, within 15 bases, within 10 bases, etc.).

In some embodiments, oligonucleotide primers are provided for amplification of a region of a BTK nucleic acid encompassing a portion that encodes for position 316 or BTK. In some embodiments, probes (e.g., with detectable labels) are provided that hybridize to BTK nucleic acids encoding a polypeptide having a substitution at position 316, but not to wild-type 316. In some embodiments, primers and/or probes (e.g., with detectable labels) are provided that hybridize to wild-type BTK nucleic acids but not to those encoding a polypeptide having a substitution at position 316. In some embodiments, a primer or probe binds to a nucleic acid encoding a polypeptide having a modification at position 316 or at a region flanking (e.g., within 100 bases, within 75 bases, within 50 bases, within 25 bases, within 20 bases, within 15 bases, within 10 bases, etc.).

In some embodiments, nucleic acids (e.g., DNA, RNA) encoding BTK polypeptides (e.g., harboring a BTK inhibitor resistance mutation (e.g., mutation from wild-type at position 316), etc.) are isolated, amplified, purified, detected, quantified, etc. by the methods and reagents provided herein. Suitable reagents for detection and/or quantification of such nucleic acids may comprise primers (e.g., for amplification, reverse transcription, etc.) or probes (e.g.; detectably-labeled (e.g., optically-labeled, fluorescently labeled, etc.) oligonucleotides) that bind (e.g., specifically). In such embodiments, detection and/or quantification may be achieved by, for example, RT-PCR, qPCR, Northern blot analysis, an enzymatic cleavage assay (e.g., INVADER, Hologic, Inc.; See e.g., U.S. Pat. Nos. 5,846,717, 6,090,543; 6,001,567; 5,985,557; and 5,994,069; each of which is herein incorporated by reference), a hybridization assay (e.g., TaqMan assay (Life Technologies; See e.g., U.S. Pat. Nos. 5,962,233 and 5,538,848, each of which is herein incorporated by reference), etc.

In some embodiments, reverse-transcriptase PCR (RT-PCR) is used to detect the expression of RNA (e.g., BTK RNA), In RT-PCR, RNA is enzymatically converted to complementary DNA or "cDNA" using a reverse transcriptase enzyme. In some embodiments, BTK cDNA is provided. The BTK comprises 18 introns which are present in BTK genomic DNA, but not present in BTK mRNA, thus, BTK cDNA is not naturally occurring (i.e., not a naturally-occurring sequence). In some embodiments, cDNA is used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In some embodiments, quantitative PCR (qPCR) or real time PCR (RT-PCR) is used to detect/quantify analytes (e.g., BTK nucleic acid sequences). In some embodiments, mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR produces an absolute measurement such as number of copies of mRNA in a sample or portion of a sample.

Other PCR-based techniques that may find use in embodiments herein include allele-specific PCR, Locked nucleic acid (LNA) PCR, etc.

In some embodiments, a BTK nucleic acid is detected by a probe-based assay, such as assays utilizing fluorescence in situ hybridization (FISH) and/or single nucleotide polymorphism (SNP) arrays.

In some embodiments, nucleic acid from a sample is sequenced (e.g., in order to detect biomarkers). Nucleic acid molecules may be sequence analyzed by any number of techniques. The analysis may identify the sequence of all or a part of a nucleic acid. Illustrative non-limiting examples of nucleic acid sequencing techniques include, but are not limited to, chain terminator (Sanger) sequencing and dye terminator sequencing, as well as "next generation" sequencing techniques. In some embodiments, RNA is reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the systems, devices, and methods employ parallel sequencing of partitioned amplicons (PCT Publication No: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties) the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties) and the Adessi PCR colony technology (Adessi et al, (2000). Nucleic Acid Res, 28, F87; WO 00018957; herein incorporated by reference in its entirety).

A set of methods referred to as "next-generation sequencing" techniques have emerged as alternatives to Sanger and dye-terminator sequencing methods (Voelkerding of al., Clinical Chem., 55: 641-658, 2009; MacLean et al., Nature Rev. Microbial., 7: 287-296; each herein incorporated by reference in their entirety). Next-generation sequencing (NGS) methods share the common feature of massively parallel, high-throughput strategies, with the goal of lower costs in comparison to older sequencing methods, NGS methods can be broadly divided into those that require template amplification and those that do not. Amplification-requiring methods include pyrosequencing commercialized by Roche as the 454 technology platforms (e.g., GS 20 and GS FLX), MiSeq, HiSeq and NextSeq platforms commercialized by Illumina, etc. Non-amplification approaches, also known as single-molecule sequencing, are exemplified by the HeliScope platform commercialized by Helicos Biosciences, Pacific Biosciences (PAC BIO RS II) and other platforms commercialized and third-generation sequencing platforms.

Certain embodiments herein comprise the detection of a BTK polypeptide (e.g., a BTK protein harboring a non-wild-type amino acid at position 316). In some embodiments of the methods, the method further comprises isolating BTK polypeptide from a biological sample.

In some embodiments, reagents are provide that bind to BTK polypeptides having the wild-type threonine at position 316. In some embodiments, reagents are provide that bind to BTK polypeptides having a substitution at position 316. Such reagents are selected from antibodies, antibody fragments, aptamers, etc.

In some embodiments, the detection method includes an enzyme/substrate combination that generates a detectable signal that corresponds to the biomarker level (e.g., using the techniques of ELISA. Western blotting, isoelectric focusing). Generally, the enzyme catalyzes a chemical alteration of the chromogenic substrate which can be measured using various techniques, including spectrophotometry, fluorescence, and chemiluminescence. Suitable enzymes include, for example, luciferases, luciferin, malate dehydrogenase, urease, horseradish peroxidase (HRPO), alkaline phosphatase, beta-galactosidase, glucoamylase, lysozyme, glucose oxidase, galactose oxidase, and glucose-6-phosphate dehydrogenase, uricase, xanthine oxidase, lactoperoxidase, microperoxidase, and the like.

In some embodiments, the detection method is a combination of fluorescence, chemiluminescence, radionuclide or enzyme/substrate combinations that generate a measurable signal. In some embodiments, multimodal signaling has unique and advantageous characteristics in biomarker assay formats.

In some embodiments, the BTK biomarker presence/levels is detected using any analytical methods including, singleplex aptamer assays, multiplexed aptamer assays, singleplex or multiplexed immunoassays, expression profiling, mass spectrometric analysis, histological/cytological methods, etc. as discussed below.

In some embodiments, BTK polypeptides (e.g., harboring a modification at position 316) are detected/quantified using a suitable immunoassay. Immunoassay methods are based on the reaction of an antibody to its corresponding target or analyte and can detect the analyte in a sample depending on the specific assay format. To improve specificity and sensitivity of an assay method based on immuno-reactivity, monoclonal antibodies and fragments thereof are often used because of their specific epitope recognition. Polyclonal antibodies have also been successfully used in various immunoassays because of their increased affinity for the target as compared to monoclonal antibodies. Immunoassays have been designed for use with a wide range of biological sample matrices. Immunoassay formats have been designed to provide qualitative, semi-quantitative, and quantitative results.

Quantitative results are generated through the use of a standard curve created with known concentrations of the specific analyte to be detected. The response or signal from an unknown sample is plotted onto the standard curve, and a quantity or level corresponding to the target in the unknown sample is established.

Numerous immunoassay formats have been designed. ELISA or EIA can be quantitative for the detection of an analyte. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition; herein incorporated by reference in its entirety).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or for quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

In some embodiments, the results of analyses described herein (e.g., detection of BTK mutations) are analyzed and/or reported (e.g., to a patient, clinician, researcher, investigator, etc.). Results, analyses, and/or data (e.g., signature, disease score, diagnosis, recommended course, etc.) are identified and/or reported as an outcome/result of an analysis. A result may be produced by receiving or generating data (e.g., test results) and transforming the data to provide an outcome or result. An outcome or result may be determinative of an action to be taken. In some embodiments, results determined by methods described herein can be independently verified by further or repeat testing.

In some embodiments, analysis results are reported (e.g., to a health care professional (e.g., laboratory technician or manager; physician, nurse, or assistant, etc.), patient, researcher, investigator, etc.). In some embodiments, a result is provided on a peripheral, device, or component of an apparatus. For example, sometimes an outcome is provided by a printer or display. In some embodiments, an outcome is reported in the form of a report.

Generating and reporting results from the methods described herein comprises transformation of biological data (e.g., presence or level of BTK biomarkers (e.g., mutation from wild-type (e.g., mutation at position 316, etc.))) into a representation of the characteristics of a subject (e.g., likelihood of responding to BTK-inhibitor treatment, etc.). Such a representation reflects information not determinable in the absence of the method steps described herein. Converting biologic data into understandable characteristics of a subject allows actions to be taken in response such information.

In some embodiments, a downstream individual (e.g., clinician, patient, etc.), upon receiving or reviewing a report comprising one or more results determined from the analyses provided herein, will take specific steps or actions in response. For example, a decision about whether or not to treat the subject, and/or how to treat the subject is made (e.g., should a first generation BTK inhibitor be used, should a $2^{nd}$ generation BTK inhibitor (e.g., that evades resistance conferred by mutation at BTK position 316) be used, etc.).

As noted above, in some embodiments, systems and methods described herein transform data from one form into another form (e.g., from BTK biomarker presence/level to diagnostic/prognostic determination, etc.). In some embodiments, the terms "transformed", "transformation", and grammatical derivations or equivalents thereof, refer to an alteration of data from a physical starting material (e.g., biological sample, etc.) into a digital representation of the physical starting material (e.g., BTK biomarker presence/level), a condensation/representation of that starting material (e.g., likelihood of resistance to treatment with BTK inhibitor, likelihood of developing resistance to treatment with BTK inhibitor, etc.), or a recommended action (e.g., treatment with a BTK inhibitor (e.g., ibrutinib), etc.).

In some embodiments, methods are provided herein for treating a disease (e.g., cancer (e.g., a B-cell malignancy, etc.), etc.) by administering a suitable therapeutic or therapy to a subject suffering from the disease. In some embodiments, a suitable therapeutic is selected based upon analysis of the mutations described herein.

In some embodiments, treating a disease (e.g., cancer (e.g., a B-cell malignancy, etc.), etc.) comprises co-administration (e.g., of pharmaceuticals (e.g., a BTK inhibitor and a second therapeutic agent, a second generation BTK inhibitor and a second therapeutic agent, two or more non-BTK-inhibitor agents), etc.) or a combination therapy (e.g., a therapeutic agent and a second therapy). In some embodiments, methods are provided for the selection of combination therapies and/or co-administration of agents.

In some embodiments, subjects that can be treated with therapeutic and therapies, according to the methods of this invention include, for example, subjects that have been diagnosed with cancers, such as a B-cell malignancy, such as Non-Hodgkin's Lymphomas, such as chronic lymphocytic leukemia (CLL), mantle cell leukemia (MCL), follicular lymphoma (FL) and diffuse large B-cell lymphoma (DLBCL), multiple myeloma (MM), etc.

In some embodiments, subjects are treated prophylactically (e.g., to prevent onset of a disease, or to prevent reoccurrence of a disease) and/or therapeutically (e.g., to cure or reduce symptoms of a current disease). In therapeutic applications, the compositions are administered to a patient already suffering from a disease, in an amount sufficient to cure or at least partially arrest the symptoms of the disease. In prophylactic applications, compositions are administered to a patient susceptible to or otherwise at risk of a particular disease, disorder or condition (e.g., because the patient previously suffered from the disease). Such an amount is defined to be a "prophylactically effective amount or dose." In this use, the precise amounts also depend on the patient's state of health, weight, and the like. Effective amounts for these uses will depend on the severity and course of the disease, disorder or condition, previous therapy, the patient's health status and response to the drugs, and the judgment of the treating clinician.

In some embodiments, a subject is treated for cancer (e.g., a B-cell malignancy) with chemotherapy. Many chemotherapeutics are presently known in the art and can be used in embodiments herein. In some embodiments, the chemotherapeutic is selected from the group consisting of mitotic inhibitors, alkylating agents, anti-metabolites, intercalating antibiotics, growth factor inhibitors, cell cycle inhibitors, enzyme inhibitors, topoisomerase inhibitors, protein-protein interaction inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Some embodiments comprise the administration of anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

In some embodiments, multiple chemotherapeutics are co-administered. In some embodiments, co-administration of multiple therapies/therapeutics is particularly indicated when resistance to one or more therapeutics (e.g., a BTK inhibitor (e.g., ibrutinib), etc.) is predicted. In some embodiments, analysis of a subject (or a sample from a subject) indicates/determines that the subject is resistant, at risk for resistance, or likely to become resistant to one or more therapeutics (e.g., a BTK inhibitor (e.g., ibrutinib), etc.). In such embodiments, the therapeutic at issue (e.g., a BTK inhibitor (e.g., ibrutinib), etc.) is avoided or is co-administered with one or more additional therapeutics to enhance the efficacy of treatment in the event of resistance.

In some embodiments, an immunotherapy or immunotherapeutic agent is administered (or co-administered) as part of a method herein. In some embodiments, an agent that finds use in embodiments herein specifically binds a component of a regulatory T cell, myeloid suppressor cell, or dendritic cell. In another aspect, the agent specifically binds one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta receptor (TGF-βR); Transforming growth factor-beta (TGF-β); Programmed Death-1 (PD-1); Programmed death-1 ligand (PD-L1 or PD-L2); Receptor activator of nuclear factor-κB (RANK); Receptor activator of nuclear factor-κB (RANK) ligand (RANKL); LAG-3; glucocorticoid-induced tumor necrosis factor receptor family-related gene (GITR; TNFRSF18); or Interleukin-4 receptor (IL-4R). In some embodiments, the agent is an agonist that increases the function of the targeted molecule. In other embodiments, the agent is an antagonist that inhibits the function of the targeted molecule. In some embodiments, an agent that finds use in embodiments herein binds a specific cytokine, cytokine receptor, co-stimulatory molecule, co-inhibitory molecule, or immunomodulatory receptor that modulates the immune system. In another aspect, the agent specifically binds one of the following molecules: tumor necrosis factor (TNF) superfamily; tumor necrosis factor-α (TNF-α); tumor necrosis factor receptor (TNFR) superfamily; Interleukin-12 (IL-12); IL-12 receptor; 4-1BB (CD137); 4-1BB ligand (4-1BBL; CD137L); OX40 (CD134; TNR4); OX40 ligand (OX40L; CD40; CD40 ligand (CD40L); CTLA-4; Programmed death-1 (PD-1); PD-1 ligand I (PD-L1: B7-H1); or PD-1 ligand 2 (PD-L2; B7-DC); B7 family; B7-1 (CD80); B7-2 (CD86); B7-H3; B7-H4; GITR/AITR: GITRL/AITRL; BTLA; CD70; CD27; LIGHT; HVEM: Toll-like receptor (TLR) (TLR 1, 2, 3, 4, 5, 6, 7, 8, 9, 10). In some embodiments, the agent is an agonist that increases the function of the targeted molecule. In other embodiments, the agent is an antagonist that inhibits the function of the targeted molecule.

In addition to employing the methods described herein (e.g., for determining potential resistance to a BTK inhibitor (e.g., ibrutinib), etc.), the particular choice of therapeutics for treatment will depend upon the diagnosis and judgment of the condition of the patient and the appropriate treatment protocol.

In some embodiments, radiation therapy is provided for inhibiting abnormal cell growth or treating a hyperproliferative disorder in the subject. Techniques for administering radiation therapy are known in the art, and these techniques can be used in embodiments described herein. Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy.

In some embodiments, treatment comprises the administration of one or more substances selected from anti-angiogenesis agents, signal transduction inhibitors, antiproliferative agents, glycolysis inhibitors, or autophagy inhibitors and apoptosis inducing agents such as ABT-199 (venetoclax)

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in methods described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In some embodiments, methods herein comprise administration of a therapeutic agent effective in treating leukemia and/or other cancers. In some embodiments, a therapeutic agent is one approved for the treatment of Chronic Lymphocytic Leukemia (CLL), for example: Alemtuzumab, AMBOCHLORIN (Chlorambucil), AMBOCLORIN (Chlorambucil), ARZERRA (Ofatumumab), Bendamustine Hydrochloride, CAMPATH (Alemtuzumab), CHLORAMBUCILCLAFEN (Cyclophosphamide), Cyclophosphamide, CYTOXAN (Cyclophosphamide), FLUDARA (Fludarabine Phosphate), Fludarabine Phosphate, LEUKERAN (Chlorambucil), LINFOLIZIN (Chlorambucil), NEOSAR (Cyclophosphamide), Ofatumumab, TREANDA (Bendamustine Hydrochloride), etc.

In some embodiments, methods herein comprise administration of one or more alkylating agents (e.g., for the treatment of cancer) selected from, for example, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, mitolactol, cisplatin, carboplatin, eptaplatin, lobaplatin, nedaplatin, oxaliplatin, and satraplatin.

In some embodiments, methods herein comprise administration of one or more anti-metabolites (e.g., for the treatment of cancer) selected from, for example, methotrexate, 6-mercaptopurineriboside, mercaptopurine, 5-fluorouracil, tegafur, doxifluridine, carmofur, cytarabine, cytarabine ocfosfate, enocitabine, gemcitabine, fludarabin, 5-azacitidine, capecitabine, cladribine, clofarabine, decitabine, eflomithine, ethynylcytidine, cytosine arabinoside, hydroxyurea, melphalan, nelarabine, nolatrexed, ocfosf[iota]te, disodium premetrexed, pentostatin, pelitrexol, raltitrexed, triapine, trimetrexate, vidarabine, vincristine, and vinorelbine;

In some embodiments, methods herein comprise administration of one or more hormonal therapy agents (e.g., for the treatment of cancer) selected from, for example, exemestane, Lupron, anastrozole, doxercalciferol, fadrozole, formestane, abiraterone acetate, finasteride, epristeride, tamoxifen citrate, fulvestrant, Trelstar, toremifene, raloxifene, lasofoxifene, letrozole, sagopilone, ixabepilone, epothilone B, vinblastine, vinflunine, docetaxel, and paclitaxel; etc.

In some embodiments, methods herein comprise administration of one or more cytotoxic topoisomerase inhibiting agents (e.g., for the treatment of cancer) selected from, for example, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, etc.

In some embodiments, methods herein comprise administration of one or more anti-angiogenic compounds (e.g., for the treatment of cancer) selected from, for example, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin.

In some embodiments, methods herein comprise administration of one or more antibodies (e.g., for the treatment of cancer) selected from, for example, trastuzumab, cetuximab, bevacizumab, rituximab, ticilimumab, ipilimumab, lumiliximab, catumaxomab, atacicept, oregovomab, and alemtuzumab.

In some embodiments, methods herein comprise administration of one or more VEGF inhibitors (e.g., for the treatment of cancer) selected from, for example, sorafenib, DAST, bevacizumab, sunitinib, recentin, axitinib, aflibercept, telatinib, brivanib alaninate, vatalanib, pazopanib, and ranibizumab.

In some embodiments, methods herein comprise administration of one or more EGFR inhibitors (e.g., for the treatment of cancer) selected from, for example, cetuximab, panitumumab, vectibix, gefitinib, erlotinib, and Zactima.

In some embodiments, methods herein comprise administration of one or more HER2 inhibitors (e.g., for the treatment of cancer) selected from, for example, lapatinib, tratuzumab, and pertuzumab; CDK inhibitor is selected from roscovitine and flavopiridol;

In some embodiments, methods herein comprise administration of one or more proteasome inhibitors (e.g., for the treatment of cancer) selected from, for example, bortezomib and carfilzomib.

In some embodiments, methods herein comprise administration of one or more serine/threonine kinase inhibitors (e.g., for the treatment of cancer), for example, MEK inhibitors and Raf inhibitors such as sorafenib.

In some embodiments, methods herein comprise administration of one or more tyrosine kinase inhibitors (e.g., for the treatment of cancer) selected from, for example, dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab and pertuzumab. Cerdulatinib and tofacitinib In some embodiments, methods herein comprise administration of one or more androgen receptor antagonists (e.g., for the treatment of cancer) selected from, for example, nandrolone decanoate, fluoxymesterone, Android, Prostaid, andromustine, bicalutamide, flutamide, apocyproterone, apoflutamide, chlormadinone acetate, Androcur, Tabi, cyproterone acetate, and nilutamide.

In some embodiments, methods herein comprise administration of one or more aromatase inhibitors (e.g., for the treatment of cancer) selected from, for example, anastrozole, letrozole, testolactone, exemestane, aminoglutethimide, and formestane.

In some embodiments, methods herein comprise administration of one or more other anti-cancer agents including, e.g., alitretinoin, ampligen, atrasentan bexarotene, bortezomib, bosentan, calcitriol, exisulind, fotemustine, ibandronic acid, miltefosine, mitoxantrone, 1-asparaginase, procarbazine, dacarbazine, hydroxycarbamide, pegaspargase, pentostatin, tazaroten, velcade, gallium nitrate, canfosfamide, darinaparsin, and tretinoin.

EXAMPLES

Example 1

Materials and Methods

Patient Samples

Research was conducted on diagnostic residual samples in accordance with the Declaration of Helsinki and institutional IRB policies. Serial samples at four time points throughout patient's disease course were studied.

Purification of CD19+ B cells and DNA Isolation

For blood and bone marrow, mononuclear cells were isolated following red cell lysis. B-cells were then enriched and purified using Dynabeads® CD19 pan B kit (Life Technologies, Oslo, Norway) with 90% purity assessed by flow cytometry. DNA was isolated using QIAamp DNA mini kit for S1 and S3 samples and QIAamp DNA FFPE Tissue kit for S2 and S4 samples.

Next Generation Sequencing (NGS)

A hybrid capture panel targeting 1,200 cancer-associated genes (Onco1K) was used to detect genomic alterations in S1 and S3. Libraries were prepared from 200 ng of isolated DNA (Kapa Biosystems), subject to hybrid capture (Roche Nimblegen) and sequenced via HiSeq 2500 (Illumina) with 21.9 and 19.3 million read pairs respectively. The BTK mutated position was sequenced at a depth of 800× in S1 and 400× in S3 in the Onco1K libraries. Targeted sequencing was performed for S1-S4 at an average depth of 2300× using a 17-gene amplicon-based CLL panel. Deeper targeted-sequencing of BTK was performed for S1 and S2 samples at depth of 6,200× and 3,700× respectively using the CLL panel. In this assay, multiplex PCR was done with 10 ng DNA, libraries were prepared (Kapa Biosystems), and sequenced via MiSeq (Illumina).

NGS Data Analysis

Data analysis for both panels was performed on a HIPAA-compliant high performance computing system (Center for Research Informatics, The University of Chicago) using in-house developed bioinformatics pipelines, with variant detection performed at a threshold of 10% mutant allelic fraction (MAF) for Onco1K and 5% for CLL Panel. ~22 million read pairs were sequenced per library. The informatics pipeline included quality checks (FastQC) and adapter trimming, followed by alignment using Burrows-Wheeler Aligner and Indel-realignment. The point mutations and small indels were detected using a combination of Samtools pileup and an in-house pileup analyzer toolkit. Amplicon Indel Hunter was used for indel detection in CLL Panel. The resulting mutations were annotated using Alamut. Additional filters were used on the annotated files based on 1000G frequencies (to remove inherited SNPs), SIFT predictions and coding effects to return a final list of somatic mutations (54 in S1 and 56 in S3) by large panel.

Sanger Sequencing

The presence of $BTK^{T316A}$ mutation was confirmed using Sanger sequencing. Primers (Forward primer: 5'GAGACAGAGGAAGTGGGACG 3' Reverse primer: 5'GCACCACTTCCTCCTACAGA 3') were designed to amplify exon 11 of BTK encompassing the mutation. The polymerase chain reaction (PCR) product of 217 bp was subjected to Sanger sequencing.

Structural Analysis

PyMOL was used to analyze the domain structures of BTK, including PH domain and TH domain (PDB code=1BTK), SH3 domain (1QLY), SH2 domain (2GE9), and kinase domain (3GEN).

Generation of BTK C481S and T316A Mutant Constructs

BTK WT cDNA clone in pCMV6 expression vector was purchased from ORIGENE (Rockville, Md. USA). $BTK^{C481S}$ and $BTK^{T316A}$ mutant vectors were generated using QuikChange II Site-Directed Mutagenesis Kit (Agilent Technologies, Cedar Creek, Tex., USA) following manufacturer's instructions. The identity of the mutant constructs was confirmed by Sanger sequencing.

Cell Transfection

TMD8 cells were transfected with constructs of BTK WT or $BTK^{C481S}$ and $BTK^{T316A}$ mutants using Amaxa Nucleofection technology, according to the manufacturer's protocols (Amaxa, Cologne, Germany; kit V, Program U-13). After transfection, the cells were co-cultured with NKTert cells in a 24-well plate for 24 hr for recovery. Ibr or vehicle was then added into the transfected TMD8 cells and cellular viability was determined with Muse™ Count & Viability kit using Muse Cell Analyzer (Millipore, Hayward, Calif.).

Cell Cycle Analysis

BTK WT or mutant-transfected TMD8 cells were treated with ibr for 72 hrs at indicated doses. Cells were then exposed to 10 μM BrdU for 2 hrs followed by cell cycle analysis according to the manufacturer's instructions using BrdU Flow Kit (BD Pharmingen, San Diego, Calif., USA). Flow cytometric analysis was performed using 4-laser BD LSR II using FACSDiva and FlowJo software.

Intracellular Phospho-Flow Staining and Flow Cytometry Analysis

Intracellular phospho-flow assay was conducted. $1\times10^6$ BTK WT- or mutant-transfected TMD8 cells were treated with 100 nM ibr for 1 hr at 37° C. and followed by stimulation of 5 μg/mL of goat F(ab')2 anti-human IgM/IgG (Southern Biotech, Birmingham, Ala. USA) for 15 min. Cells were then fixed in 4% formaldehyde for 10 min and permeabilized with 100% methanol for 20 min, and were subjected to staining with Alexa Fluor® 647-anti-phospho-AKT (Ser473), Alexa Fluor® 488 anti-phospho-ERK1/2 (Thr202/Tyr204) (Cell Signaling, Billerica, Mass. USA), PE-anti-phospho-PLCγ2 (Tyr759), and PE-anti-phospho-BTK (Tyr223) (BD Bioscience, Franklin Lakes, N.J.). Flow cytometry was performed with BD™ LSR II flow cytometer and data analyzed with FlowJo v10.

Example 2

Results

Ibrutinib (ibr), a first-in-class BTK inhibitor, has demonstrated high response rates in both relapsed/refractory and treatment naïve chronic lymphocytic leukemia (CLL) (refs. 1, 2; incorporated by reference in their entireties). However, about 25% of patients discontinue ibr therapy at a median follow-up of 20 months. Notably, 40-42% of these patients stopped the treatment as a result of disease progression (refs. 2, 3; incorporated by reference in their entireties). Among progressed patients, at least half developed Richter's transformation (RT). Treatment options for these patients are limited and outcomes are dismal with a mortality rate exceeding 75% and a median overall survival (OS) of 3 months (ref 3; incorporated by reference in its entirety). As the use of ibr becomes more prevalent in CLL and other types of non-Hodgkin lymphoma (NHL), more patients are expected to develop resistance (ref 4; incorporated by reference in its entirety). Thus a complete understanding of the mechanisms of ibr resistance is clinically important for the development of strategies to prevent and treat ibr-relapsed patients.

Recent studies have provided some insights into ibr-resistance. Both $BTK^{C481S}$ and phospholipase C-γ2 (PLCG2) mutations have been identified (refs. 2, 5-6; incorporated by reference in their entireties). It has been demonstrated that substitution of cysteine 481 with serine in BTK resulted in loss of covalent ibr binding, restoration of BTK activity, and subsequent B-cell receptor (BCR) signaling that leads to clinical relapse. Since the first identification of BTK$^{C481S}$, other BTK mutations (C481F/Y/R, T474I/S, and L528W) have been associated with ibr refractory cases. However, the cause-and-effect relationships have not been established for these mutations since some of the variants were present at only 4-8% variant allele frequencies. In addition, BTK mutations have been observed in several Richter transformed patients treated with ibr. It is not clear whether BTK mutations are related to Richter transformation or ibr treatment or both. Experiments conducted during development of embodiments herein identified a patient with CLL and RT who received multiple treatments including ibr. With longitudinal sequencing analysis of four samples collected throughout the disease and treatment course, further insights were gained into the mechanisms of ibr resistance that impact the rational design of next-generation BTK inhibitors, as well as mutation detection for emerging ibr resistance.

The patient is a 57 year old woman who presented with constitutional symptoms. CBC showed mild lymphocytosis (WBC 15 K/uL, 75% lymphocytes, FIG. 1A) with typical immuno-phenotypic features of CLL (cytogenetics/FISH not available). Bone marrow assessment revealed 66% CLL cells [Specimen S1] (FIG. 1B, top left). Following an 18-month observation period, she developed worsening fatigue and cytopenias (platelets 84 K/uL; marrow with 95% CLL cells) and proceeded to receive six cycles of FCR (fludarabine, cyclophosphamide and rituximab). She achieved complete remission. However, the disease returned with manifestations of abdominal discomfort and new pelvic lymphadenopathy. A lymph node core biopsy showed ~5% large cells not associated with proliferation centers, suggestive of early Richter's transformation (RT) [S2] (FIG. 1B, bottom middle). Bone marrow aspirate demonstrated 17p deletion by FISH in 8% of cells. She was then treated with two chemoimmuno-regimens, but failed to improve (FIG. 1A). She was not deemed a candidate for allogeneic stem cell transplantation due to persistent disease/cytopenias. Thus, ibr monotherapy was initiated. The patient had a remarkable partial response that lasted 10 months. However, there was evidence of progressive disease with both worsening lymphadenopathy and lymphocytosis (91%) [S3] showing patient had RT with concurrent CLL. This prompted a change to FCO (fludarabine, cyclophosphamide, obinutuzumab) regimen. Within a week, the patient developed a large pleural effusion. Cell block revealed numerous transformed large cells representing ~40% of the cellularity [S4] (FIG. 1B bottom right). Shortly thereafter, the patient developed fever with altered mental status and subsequently expired. Longitudinally, four samples had been collected from the patient: S1, bone marrow collected at initial diagnosis (time 0); S2, lymph node core biopsy at RT progression (time 0+76 months, prior to ibr Rx); S3, peripheral blood following ibr failure (time 0+89 months); and S4, cell block of pleural fluid (time 0+90 months).

Figure 5:
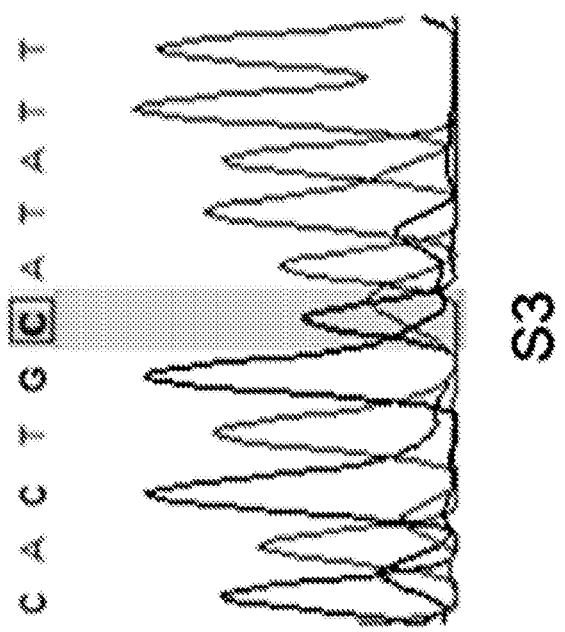
FIG. 5. Sanger sequencing confirmation of BTK T316A mutation in S1 (CLL diagnosis) and S3 (Post-ibr CLL relapse). Primers were designed to amplify exon 11 of BTK. The BTK mutated position is highlighted in blue.
Figure 5:
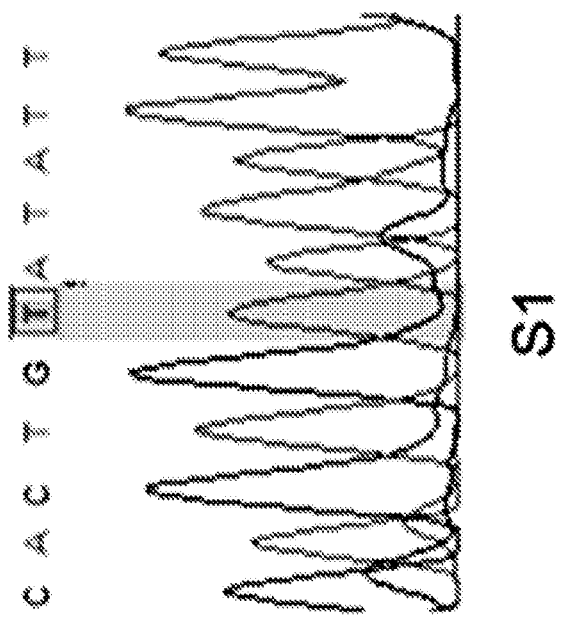

To understand genetic mechanisms underlying ibr resistance developed in this patient, the S1 (Dx) and S3 (Ibr failure) samples were sequenced using Onco1K, a 1,200-gene panel with an average sequencing depth of 420×. Fifty-four and 56 somatic variants were identified in S1 and S3, respectively. Comparison of the two samples revealed several relapse-specific mutations in: BTK, ZMYM3, MLLT6, and SDHA. Among these, a novel BTK missense mutation T316A (Nucleotide c.946T>C, NM_000061) was detected in 75% of reads in S3 but not in S1. Sanger sequencing confirmed the presence and absence of this mutation in the two samples (FIG. 5).

To determine whether this mutation had emerged at the time of Richter transformation, S1 (Dx) and S2 (RT) samples were deep-sequenced using a dedicated 17-gene CLL panel (ATM, CXCR4, MYD88, SF3B1, BCOR, FAT3, NOTCH1 SPEN, BIRC3, FBXW7, NRAS, TP53, BRAF, KRAS, PLCG2, XPO1, and BTK). With a sequencing depth of 3,700×, BTK$^{T316A}$ was not detected in the RT lymph node (S2, with ~5% large cell involvement) indicating that most of the large transformed cells do not carry this mutation. Pairwise comparison of mutations in the 17 genes between S1, S2, S3 and S4 was also performed (FIG. 1C). BTK mutation was the only variant that is present in S3 and S4 ibr-relapsed CLL samples, while absent in S1 and S2 which is the RT diagnostic lymph node.

Figure 2:
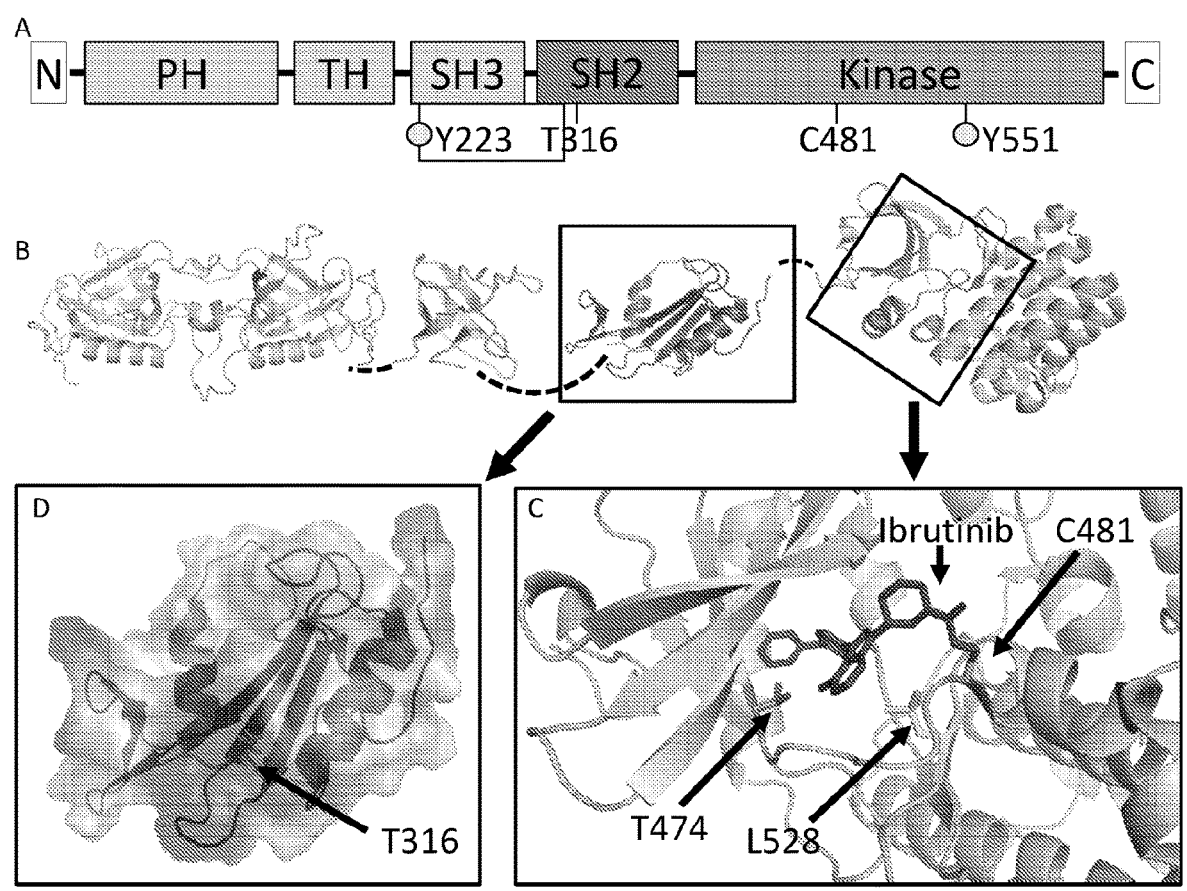
FIG. 2. $BTK^{T316A}$ is a structurally novel mutation located in the SH2 domain of BTK not directly interfering with ibr binding. (A) Schematic representation of BTK domain organization. Five domains: PH, pleckstrin homology; TH, TEC homology; SH3, SRC homology 3; SH2, SRC homology 2 and kinase domain. Y223 and Y551 are tyrosine phosphorylation sites. (B) Structures of BTK domains. The unsolved interdomain areas are denoted by broken lines. (C) Enlarged view of the kinase domain with ibr binding. The three reported mutations sites are shown. C481 forms a covalent bond with ibr, which is disrupted by C481 mutations. T474 and L528 are also located at the ibr binding pocket and mutations at these sites are expected to weaken (T474I) or hinder (L528W) ibr binding. (D) Enlarged view of the SH2 domain with electrostatic surface potential. T316 is at the center of the positively-charged binding pocket, which is predicted to interact with phosphotyrosine residues.

To better understand how T316A and other reported BTK variants involving residues C481, T474, and L528 confers ibr resistance, these mutations were mapped onto the available BTK domain structures (refs. 2, 5, 7-10; incorporated by reference in their entireties). Although the role of C481, which is covalently linked to ibr, is better understood (refs. 5, 11; incorporated by reference in their entireties), T474 and L528 have never been structurally or functionally characterized. Structural modeling revealed that along with C481, T474 and L528 are located in the kinase domain at the ibr docking site where the mutations either directly attenuate (T474I/S) or hinder (L528W) ibr binding (FIG. 2 A-C).

In contrast to the kinase domain mutations, T316 is located at the center of the positively-charged binding pocket in the Src-homology 2 (SH2) domain responsible for interacting with phosphotyrosine-containing peptide substrates (FIG. 2D). The major binding partner of BTK SH2 domain is B-cell linker protein (BLNK), and this interaction is essential for the phosphorylation and activation of the downstream substrate PLCG2 (ref 12; incorporated by reference in its entirety). The threonine to alanine substitution prevents key contact to phosphotyrosine, thus may lessen affinity of BTK for BLNK or other BTK partner proteins.

Figure 3:
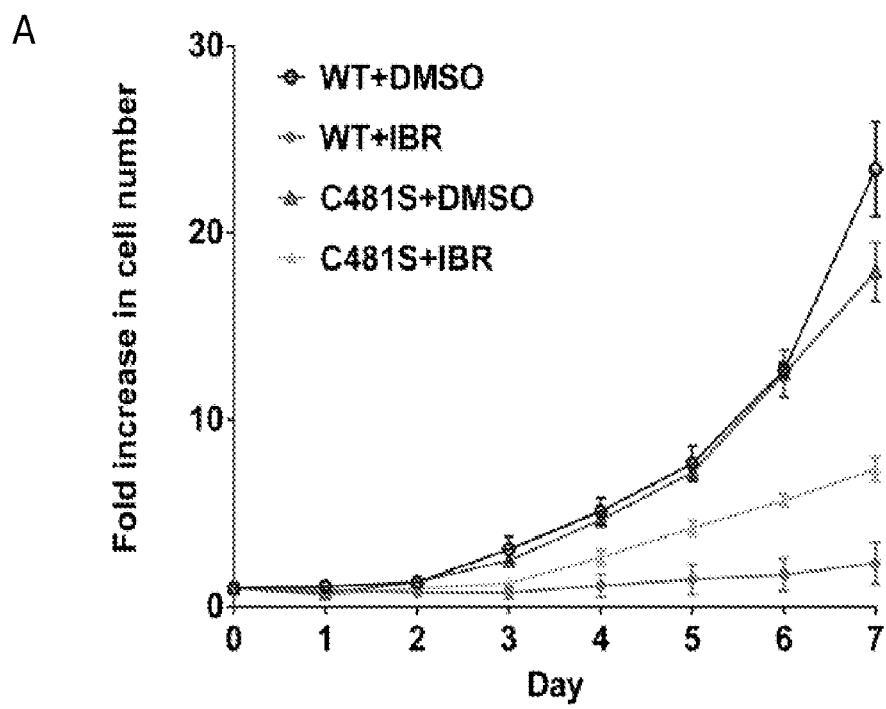
FIG. 3. T316A mutation functionally confers ibr resistance at the cellular level. (A) Growth of TMD8 cells transfected with BTK T316A, C481S, and WT BTK constructs. The transfected cells were cultured with either 100 nM ibr or DMSO. The live cell numbers were counted daily to 7 days. The results represent four independent experiments. (B) Cell proliferation evaluated with the BrdU incorporation assay. Cells transfected with WT BTK and T316A were treated with 100 nM ibr for 3 days and were labeled with 10 μM BrdU for 2 hrs.
Figure 3:
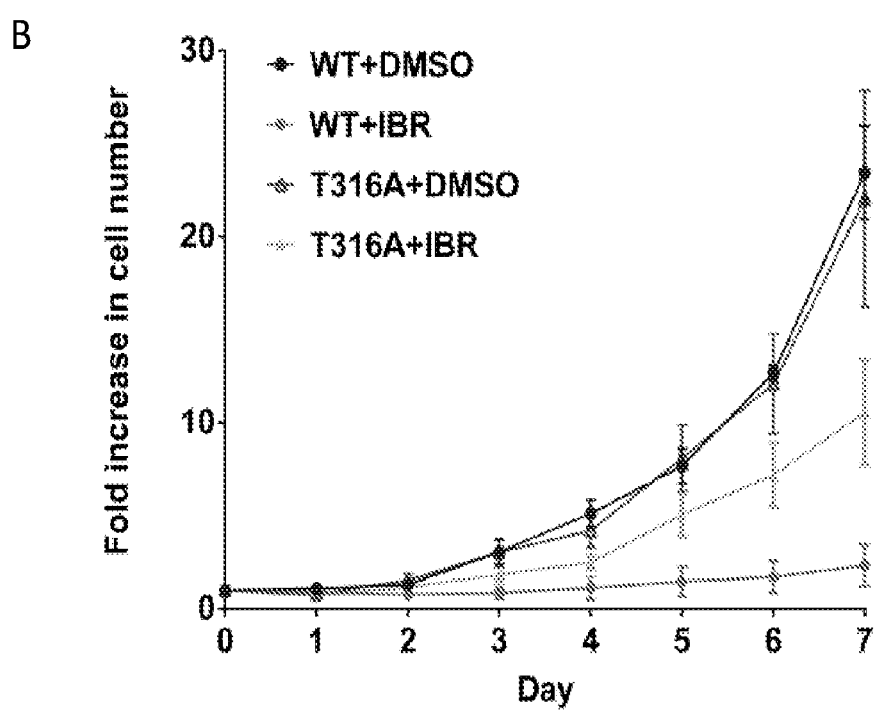
Figure 3:
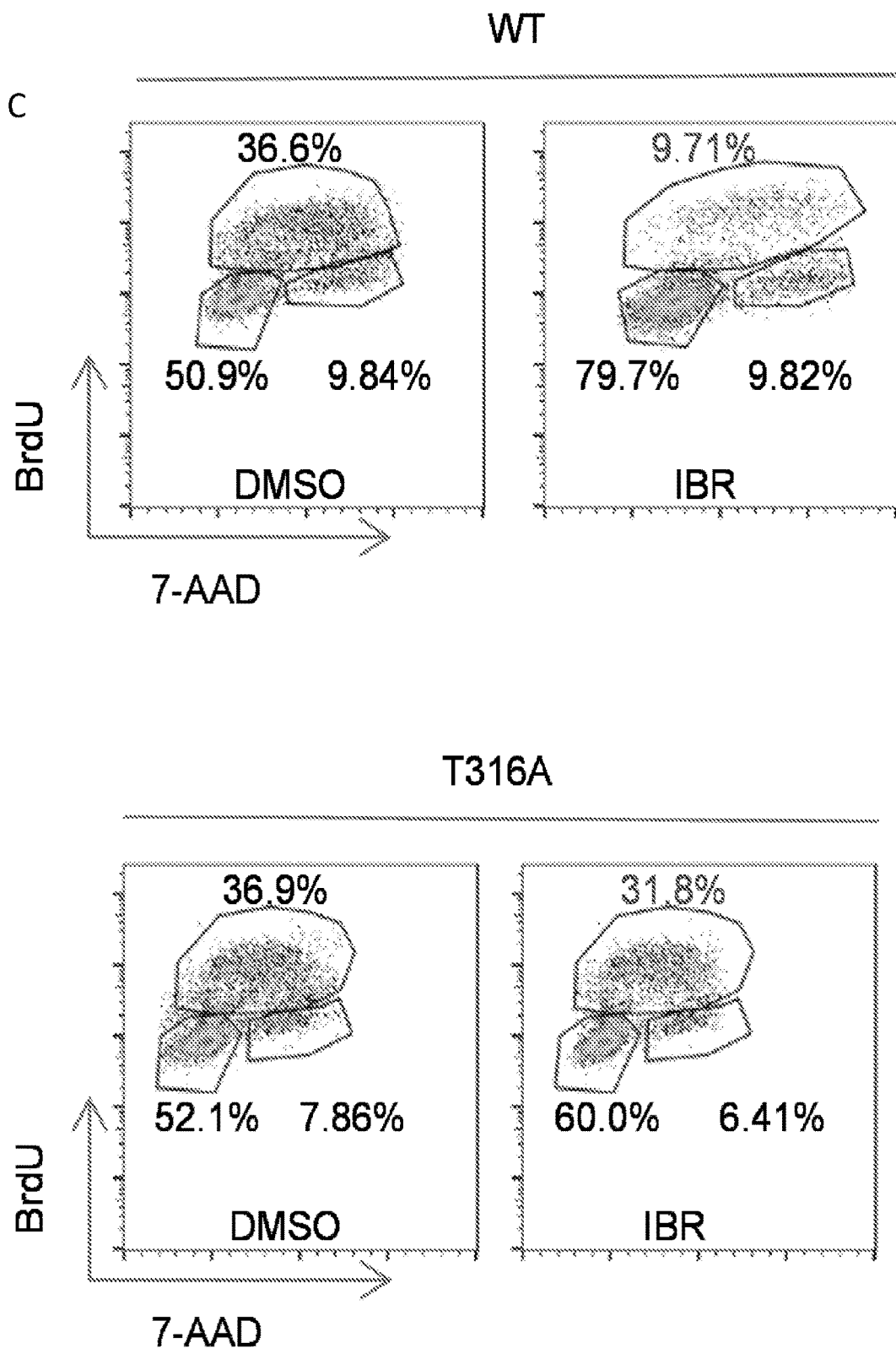

Unlike kinase domain mutations, T316A, located in the SH2 domain, does not directly interfere with ibr binding. The functional impact of T316A mutation was assessed at the cellular levels. BTK wild type (WT) and T316A as well as C481S expression vectors were constructed and transfected into an ibr-sensitive lymphoma cell line (TMD8) and cell growth was followed. As shown in FIGS. 3A&B, cell growth was severely inhibited with 100 nM ibr in cells transfected with WT BTK, whereas continued cell growth was observed in BTK$^{T316A}$- or BTK$^{C481S}$-transfected cells (FIGS. 3A&B), demonstrating that the T316A mutation is able to trounce ibr inhibition at a comparable level to the C481S mutation. These results were confirmed with the BrdU incorporation assay that showed ibr inhibition of cellular proliferation was significantly lost in cells bearing BTK$^{T316A}$ compared to cells bearing WT BTK (FIG. 3C, 31.8% vs 9.71%).

Figure 4:
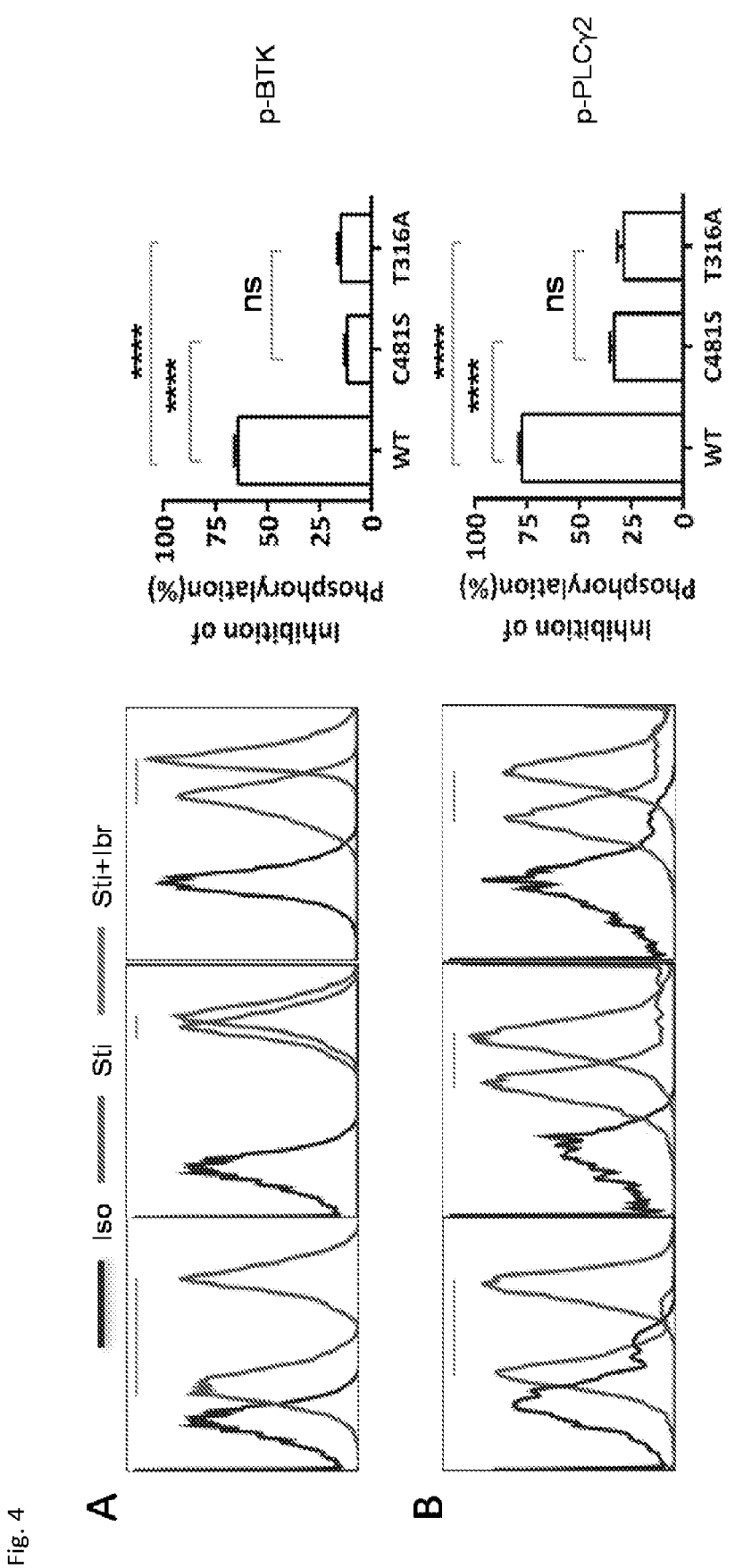
FIG. 4. T316A mutation functionally confers ibr resistance at the molecular level. Intracellular protein phosphorylation was measured at day 4 after TMD8 transfection. Iso, isotype control. Sti, Cells were stimulated with anti-IgG/IgM antibodies for 10 minutes before analysis. Sti+Ibr, Cells were treated with 100 nM ibr for 1 hour before stimulation with anti-IgG/IgM antibodies for 10 minutes. Left panels, representative analyses. Right panel, aggregate data for three repeat analyses. Inhibition of phosphorylaton (%) is calculated as $(F_{Sti}-F_{Sti+Ibr})/(F_{Sti}-F_{iso})\times 100\%$, where F denotes mean fluorescent intensity of 10,000 events. Data were analyzed using one-way ANOVA test and graphed with prism 5 GraphPad. (A) p-BTK (Y223), (B) p-PLCγ2 (Y759), (C) p-AKT (S473), and (D) p-ERK (T202/Y204).
Figure 4:
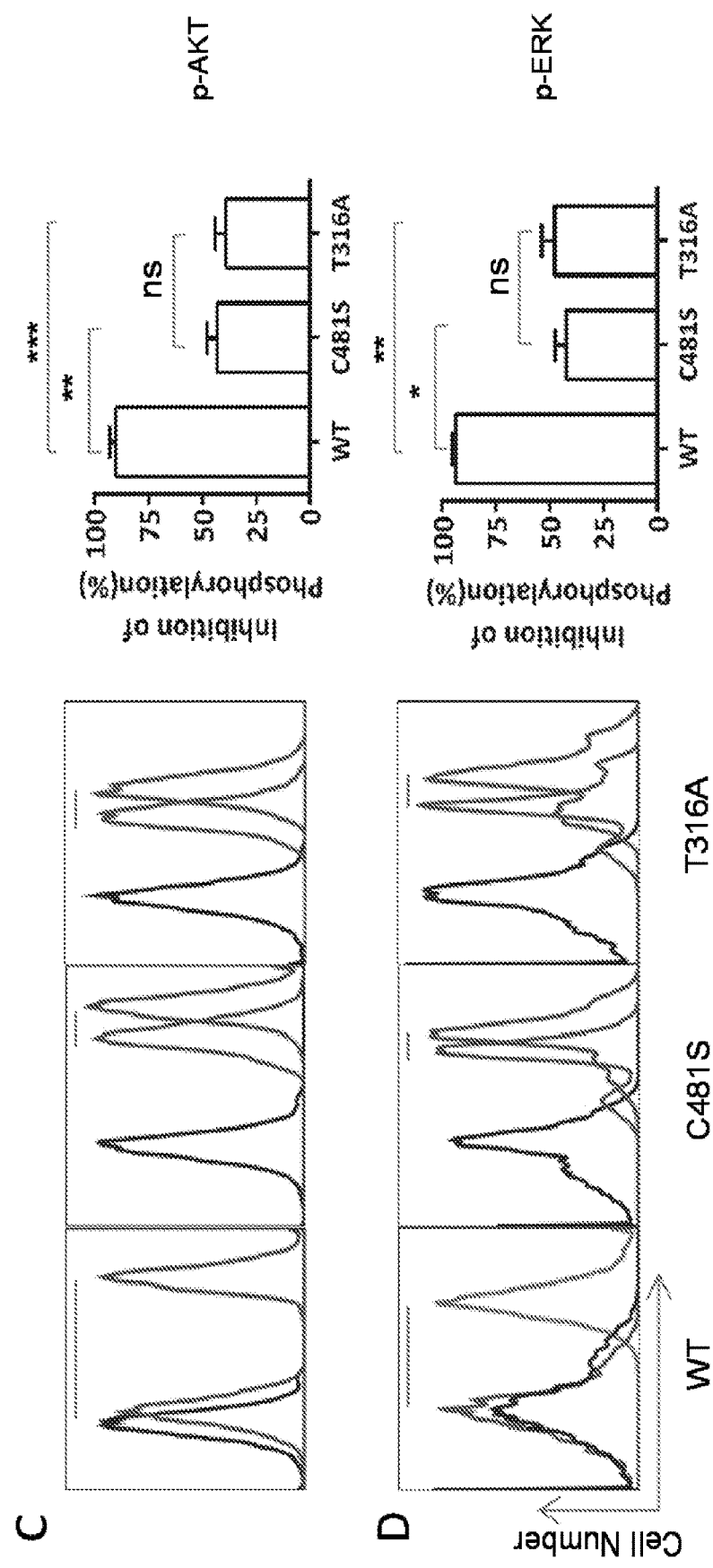

To further understand the molecular mechanisms underlying ibr-resistance caused by BTK$^{T316A}$, activity of several key players in the BCR and downstream signaling pathways were measured with phospho-flow assays. Shown in FIG. 4A, while p-BTK (Y223) in WT-transfected cells was markedly inhibited by ibrutinib, there remained a significant level of p-BTK in either the C481S or T316A-bearing cells (FIG. 4A. compare shifts from red to green, WT vs. C481S vs. T316A column). The degree of phosphorylation inhibition following ibr treatment was significantly less in C481S and T316A mutant cells than in WT cells (FIG. 4A right panel). When PLCγ2, the substrate of BTK kinase was measured, a similar pattern was observed. The degree of p-PLCγ2 inhibition by ibr was significantly diminished in both C481S and T316A-mutant cells (FIG. 4B). Moreover, resistance to ibr inhibition was reflected further downstream in p-AKT and p-ERK (FIGS. 4C&D). Collectively, results from these multiple assays demonstrate that BCR and downstream signaling pathways were not effectively inhibited by ibr in T316A mutant cells. Together with the cellular experiments of transfected cells (FIG. 3), the data firmly established that the BTK$^{T316A}$ mutant is as capable as BTK$^{C481S}$ to confer ibr resistance from a functional perspective at both cellular and molecular levels.

A BTK SH2 mutation was identified in a patient who progressed from CLL to RT, responded to ibr and then relapsed. With deep sequencing, the mutation was detected only in ibr-relapsed samples, but not in the RT LN specimen with apparent large tumor cells. This observation indicates that the BTK mutation does not contribute to the process of transformation in this case. This finding is consistent with a previous report suggesting BTK mutations are not associated with RT as only 2 of 9 such patients carried BTK or PLCG2 mutations after ibr treatment. Summarizing all 14 CLL patients reported so far, BTK mutations are only detected in patients exposed to ibr. There is not a single case that BTK mutations were identified in patients who have not received ibr (refs. 1, 2, 5; incorporated by reference in their entireties).

In some embodiments, methods herein provide mutation detection in ibr-relapsed patients. In some embodiments, for management of ibr relapsed/resistant CLL, mutation detection of BTK includes all exons, not just those encoding the kinase domain. In some embodiments, techniques for detecting BTK mutations must detect even a minute mutant clone evolving during ibr treatment, and therefore must be a highly sensitive technique for clinical early detection.

4. Zhang, S. Q., Smith, S. M., Zhang, S. Y. & Lynn Wang, Y. Mechanisms of ibrutinib resistance in chronic lymphocytic leukaemia and non-Hodgkin lymphoma. Br J Haematol 170, 445-456 (2015).
5. Furman, R. R., et al. Ibrutinib resistance in chronic lymphocytic leukemia. N Engl J Med 370, 2352-2354 (2014).
6. Woyach, J. A., et al. Resistance mechanisms for the Bruton's tyrosine kinase inhibitor ibrutinib. N Engl J Med 370, 2286-2294 (2014).
7. Hyvonen, M. & Saraste, M. Structure of the PH domain and Btk motif from Bruton's tyrosine kinase: molecular explanations for X-linked agammaglobulinaemia. The EMBO journal 16, 3396-3404 (1997).
8. Tzeng, S. R., Lou, Y. C., Pai, M. T., Jain, M. L. & Cheng, J. W. Solution structure of the human BTK SH3 domain complexed with a proline-rich peptide from p120cbl. Journal of biomolecular NMR 16, 303-312 (2000).
9. Huang, K. C., Cheng, H. T., Pai, M. T., Tzeng, S. R. & Cheng, J. W. Solution structure and phosphopeptide binding of the SH2 domain from the human Bruton's tyrosine kinase. Journal of biomolecular NMR 36, 73-78 (2006).
10. Marcotte, D. J., et al. Structures of human Bruton's tyrosine kinase in active and inactive conformations suggest a mechanism of activation for TEC family kinases. Protein science: a publication of the Protein Society 19, 429-439 (2010).
11. Cheng, S., et al. Functional characterization of BTK (C481S) mutation that confers ibrutinib resistance: exploration of alternative kinase inhibitors. Leukemia 29, 895-900 (2015).
12. Hashimoto, S., et al. Identification of the SH2 domain binding protein of Bruton's tyrosine kinase as BLNK—functional significance of Btk-SH2 domain in B-cell antigen receptor-coupled calcium signaling. Blood 94, 2357-2364 (1999).

SEQUENCES

```
                                                             SEQ ID NO: 1
  1   maavilesif   lkrsqqkkkt   splnfkkrlf   lltvhklsyy   eydfergrrg   skkgsidvek 61   itcvetvvpe   knppperqip   rrgeesseme   qisiierfpy   pfqvvydegp   lyvfspteel 121   rkrwihqlkn   virynsdlvq   kyhpcfwidg   qylccsqtak   namgcqilen   rngslkpgss 181   hrktkkplpp   tpeedqilkk   plppepaaap   vstselkkvv   alydympmna   ndlqlrkgde 241   yfileesnlp   wwrardkngq   egyipsnyvt   eaedsiemye   wyskhmtrsq   aeqllkqegk 301   eggfivrdss   kagkytvsvf   akstgdpqgv   irhyvvcstp   qsqyylaekh   lfstipelin 361   yhqhnsagli   srlkypvsqq   nknapstagl   gygsweidpk   dltflkelgt   gqfgvvkygk 421   wrgqydvaik   mikegsmsed   efieeakvmm   nlsheklvql   ygvctkqrpi   fiiteymang 481   cllnylremr   hrfqtqqlle   mckdvceame   yleskqflhr   dlaarnclvn   dqgvvkvsdf 541   glsryvldde   ytssvgskfp   vrwsppevlm   yskfssksdi   wafgvlmwei   yslgkmpyer 601   ftnsetaehi   aqglrlyrph   lasekvytim   yscwhekade   rptfkillsn   ildvmdees
```

REFERENCES

The following references, some of which are cited above by number, are herein incorporated by reference in their entireties.
1. Byrd, J. C., O'Brien, S. & James, D. F. Ibrutinib in relapsed chronic lymphocytic leukemia. N Engl J Med 369, 1278-1279 (2013).
2. Maddocks, K. J., et al. Etiology of ibrutinib therapy discontinuation and outcomes in patients with chronic lymphocytic leukemia. JAMA oncology 1, 80-87 (2015).
3. Jain, P., et al. Outcomes of patients with chronic lymphocytic leukemia after discontinuing ibrutinib. Blood 125, 2062-2067 (2015).
13. Davis, R. E., et al. Chronic active B-cell-receptor signaling in diffuse large B-cell lymphoma. Nature 463, 88-92 (2010).
14. Komarova, N. L., Burger, J. A. & Wodarz, D. Evolution of ibrutinib resistance in chronic lymphocytic leukemia (CLL). Proceedings of the National Academy of Sciences of the United States of America 111, 13906-13911 (2014).
15. Burger, J. A., et al. Clonal evolution in patients with chronic lymphocytic leukemia (CLL) developing resistance to BTK inhibition. Blood 122, 866 (2013).

The invention claimed is:

1. A method of treating a subject for cancer, wherein the subject has previously been administered ibrutinib for treatment of the cancer, comprising (a) having a sample from the subject tested for a Bruton's Tyrosine Kinase (BTK) biomarker comprising (i) a polypeptide comprising a threonine to alanine mutation at a position corresponding to position 316 of the sequence set forth in SEQ ID NO: 1, or (ii) a nucleic acid encoding said polypeptide; and (b) administering a non-ibrutinib therapy or therapeutic to the subject when the sample tests positive for the BTK biomarker.

2. The method of claim 1, wherein the nucleic acid is a cDNA.

3. The method of claim 1, wherein the biomarker is detected using oligonucleotide primers and/or probes.

4. The method of claim 1, wherein the biomarker is detected using one or more reagents selected from antibodies, antibody fragments, and aptamers.

5. The method of claim 1, further comprising administering ibrutinib to the subject before having the sample tested for the BTK biomarker.

6. The method of claim 1, further comprising a step of obtaining the sample from the subject.

7. The method of claim 1, wherein the non-ibrutinib therapy or therapeutic is part of a combination therapy.

8. The method of claim 1, wherein the cancer is a hematologic cancer.

9. The method of claim 8, wherein the cancer is selected from the group consisting of a leukemia, a lymphoma, or a myeloma.

10. The method of claim 1, wherein the cancer is a B-cell malignancy or T-cell malignancy.

11. The method of claim 1, wherein the subject has a solid tumor.

12. The method of claim 1, wherein the subject has previously tested negative for the BTK biomarker.

13. The method of claim 1, wherein the subject was responsive to treatment with the ibrutinib upon initial administration.

14. The method of claim 1, wherein the sample comprises or is obtained from blood, serum, bone marrow, or tissue biopsies.

* * * * *